(12) United States Patent
Ruckman et al.

(10) Patent No.: US 6,331,394 B1
(45) Date of Patent: *Dec. 18, 2001

(54) NUCLEIC ACID LIGANDS TO INTEGRINS

(75) Inventors: Judy Ruckman; Larry Gold; Andrew Stephens; Nebojsa Janjic, all of Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/364,543

(22) Filed: Jul. 29, 1999

Related U.S. Application Data

(63) Continuation-in-part of application No. 09/606,477, filed on Jun. 29, 2000, which is a continuation of application No. 08/956,699, filed on Oct. 23, 1997, now Pat. No. 6,083,696, which is a continuation of application No. 08/234,997, filed on Apr. 28, 1994, now Pat. No. 5,683,867, which is a continuation-in-part of application No. 07/714,131, filed on Jun. 10, 1991, now Pat. No. 5,475,096.

(51) Int. Cl.[7] .............................. C12Q 1/68; C12P 19/34; C07H 21/02; C07H 21/04
(52) U.S. Cl. ........................ 435/6; 435/91.2; 536/23.1; 536/25.4
(58) Field of Search .................. 435/6, 91.2; 536/23.1, 536/25.4

(56) References Cited

U.S. PATENT DOCUMENTS

| | | | |
|---|---|---|---|
| 5,475,096 | * 12/1995 | Gold et al. | 536/23.1 |
| 5,683,867 | * 11/1997 | Biesecker et al. | 435/6 |
| 5,723,323 | 3/1998 | Kauffman et al. | 435/6 |

FOREIGN PATENT DOCUMENTS

| | | |
|---|---|---|
| 2 183 661 A | 6/1987 | (GB). |
| WO89/06694 | 7/1989 | (WO). |
| WO 91/19813 | 12/1991 | (WO). |
| WO92/14843 | 9/1992 | (WO). |

OTHER PUBLICATIONS

Blind et al., Proc. Natl. Acad. Sci. 96(7):3606–3610, Mar. 30, 1999.*
Joyce (1989) Gene 82:83.
Joyce & Inoue (1989) Nucleic Acids Research 17:711.
Ellington & Szostak (1990) Abstracts of papers presented at the 1990 meeting on RNA Processing, Cold Spring Harbor Laboratory, Cold Spring Harbor, NY, p. 84.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.
Szostak, "Structure and Activity of Ribozymes," in *Redesigning the Molecules of Life,* (S.A. Benner ed. Springer–Verlag Berline Heidelberg, pp. 87–113 (1988).

* cited by examiner

*Primary Examiner*—Stephanie Zitomer
(74) *Attorney, Agent, or Firm*—Swanson & Bratschun, L.L.C.

(57) ABSTRACT

Methods are described for the isolation of nucleic acid ligands to integrins using the SELEX process. SELEX is an acronym for Systematic Evolution of Ligands by EXponential enrichment. The nucleic acid ligands of the present invention are useful as therapeutic and diagnostic agents.

19 Claims, 6 Drawing Sheets

Figure 1. Binding of affinity-enriched RNA pools to immobilized $\alpha_v\beta_3$.
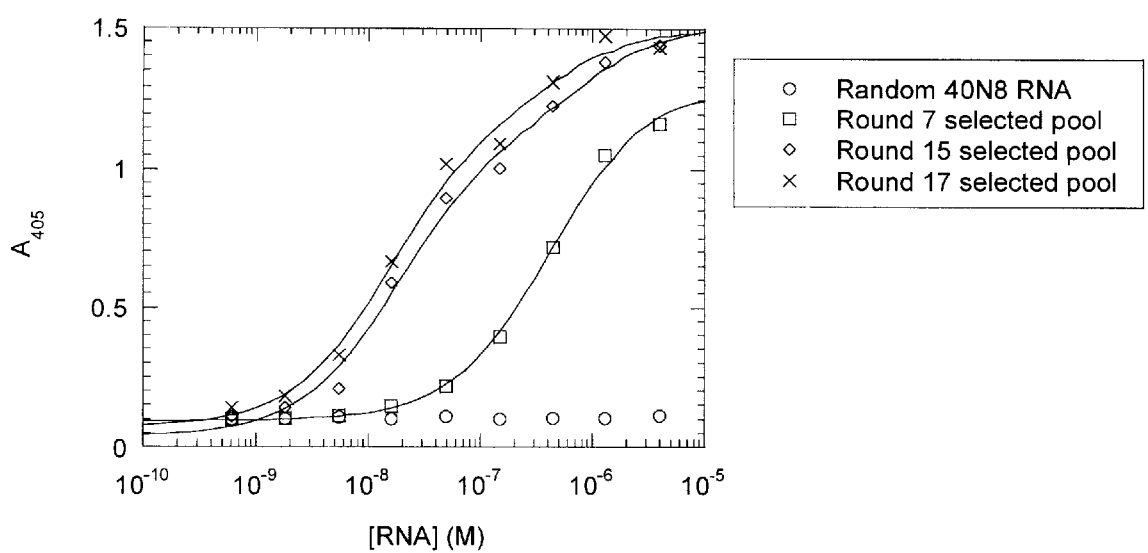

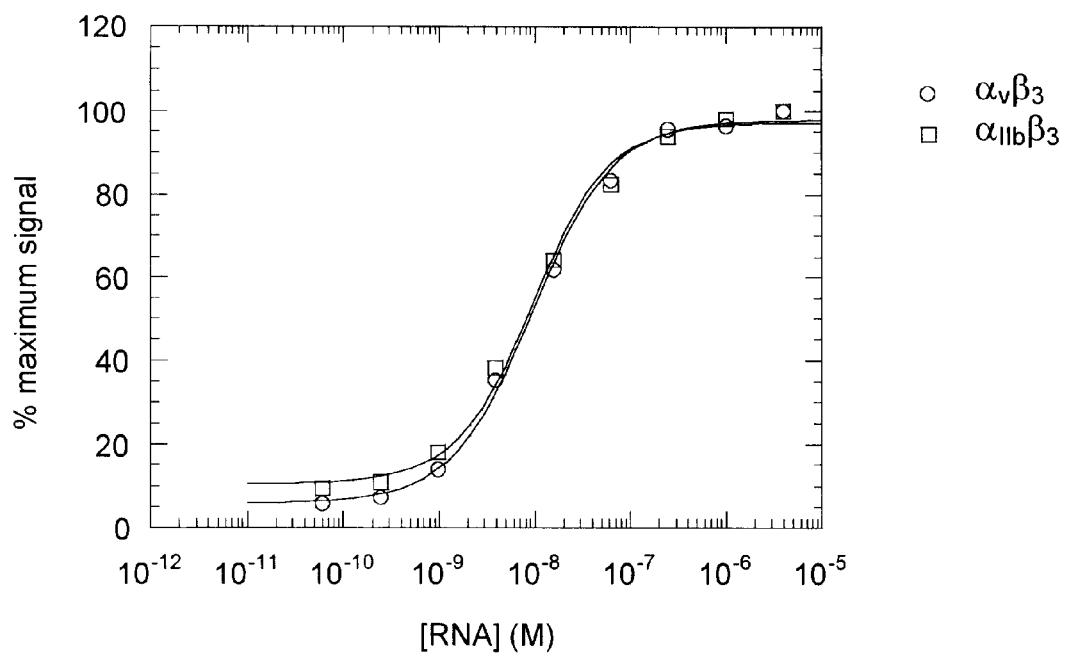
Figure 2. Cross-reactivity of aptamer 17.16 to purified integrin $\alpha_{IIb}\beta_3$.

Figure 3. Cross-reactivity of aptamer 17.16 to purified integrin $\alpha_v\beta_5$.
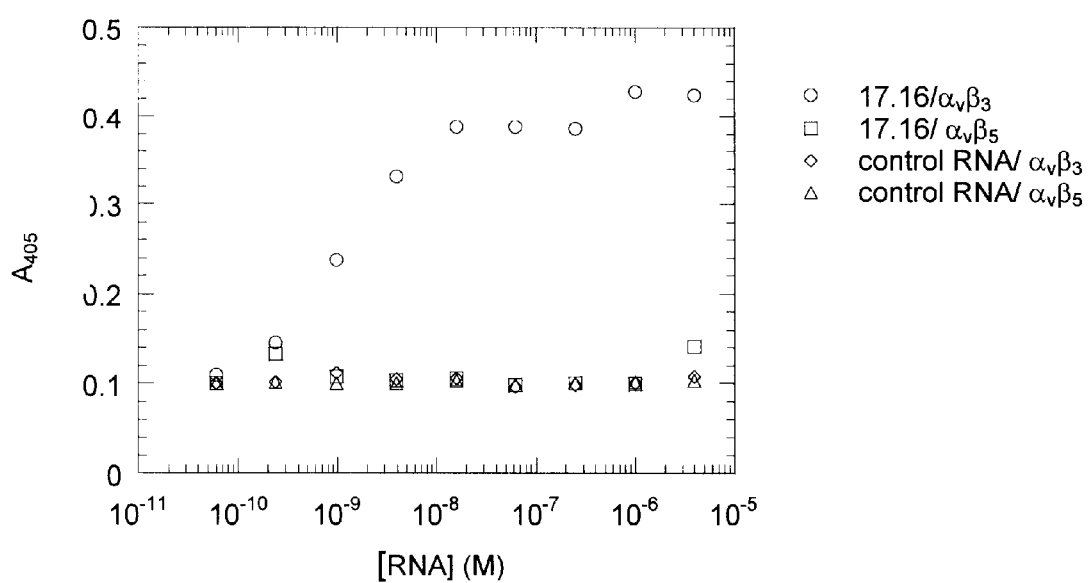

Figure 5. Binding of aptamer 17.16 to activated or resting human platelets.
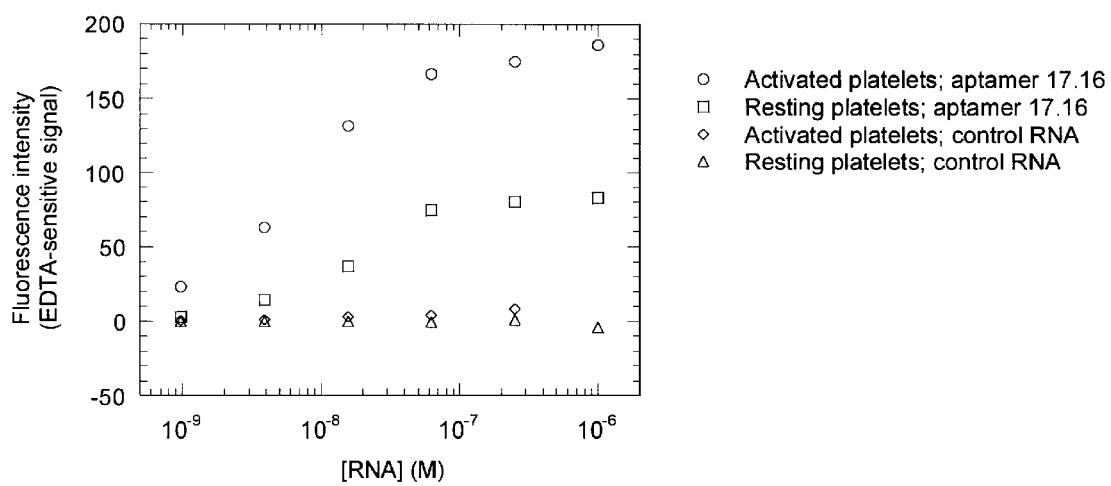

Figure 6. Biodistribution of [$^{99m}$Tc]-aptamer 17.16 or control RNA in a rabbit venous clot model.
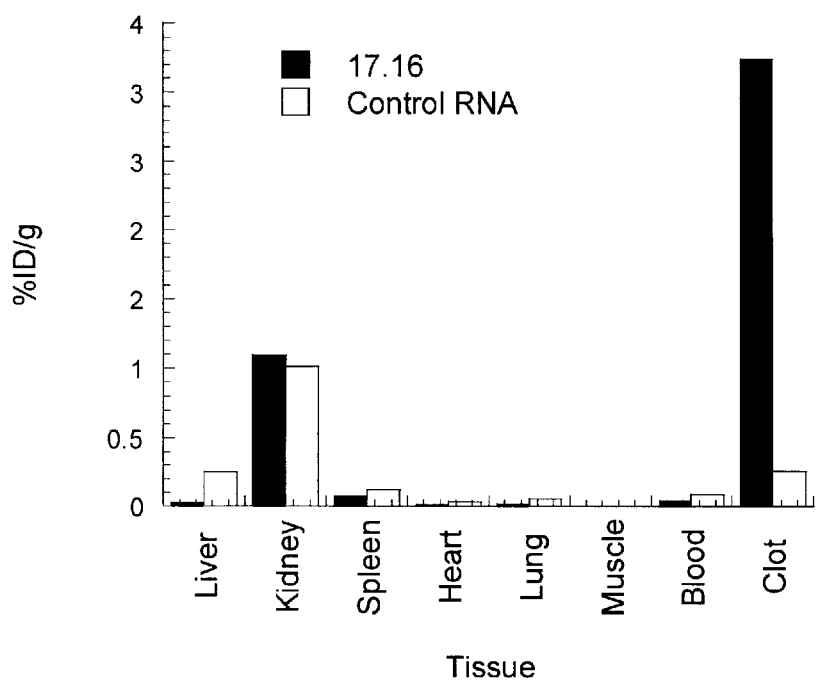

NUCLEIC ACID LIGANDS TO INTEGRINS

CROSS REFERENCE TO RELATED APPLICATIONS

This application is a Continuation-In-Part of U.S. patent application Ser. No. 09/606,477, filed Jun. 29, 2000, which is a Continuation of U.S. patent application Ser. No. 08/956,699, filed Oct. 23, 1997, now U.S. Pat. No. 6,083,696, which is a Continuation of U.S. patent application Ser. No. 08/234,997, filed Apr. 28, 1994, now U.S. Pat. No. 5,683,867, all entitled Systematic Evolution of Ligands by Exponential Enrichment: Blended SELEX. U.S. Pat. No. 5,683,867 is a Continuation-In-Part of U.S. patent application Ser. No. 07/714,131, filed Jun. 10, 1991, entitled Nucleic Acid Ligands, now U.S. Pat. No. 5,475,096.

FIELD OF THE INVENTION

This invention is directed towards nucleic acid ligands of integrins isolated using the SELEX process. SELEX is an acronym for Systematic Evolution of Ligands by EXponential Enrichment. This invention relates to integrin proteins, and methods and compositions for treating and diagnosing diseases involving integrins.

BACKGROUND OF THE INVENTION

The integrins are a class of heterodimeric integral membrane proteins, one or homologous alpha subunits and 8 homologous beta subunits associate in various combinations to yield an extensive family of receptors. Each integrin heterodimer has a large extracellular domain that mediates binding to specific ligands. These ligands may include plasma proteins, proteins expressed on the surface of adjacent cells, or components of the extracellular matrix. Several of the integrins show affinity for more than one ligand and many have overlapping specificities (Hynes (1992) Cell 69:11–25). Both the $\alpha$ and $\beta$ subunits contribute to a small intracellular domain that contacts components of the actin cytoskeleton, thus forming a physical link between proteins outside and inside the cell. Integrins play an important role in cellular adhesion and migration, and these properties are controlled by the cell, in part, by modulation of integrin affinity for its ligands (so-called "inside-out" signaling). Conversely, the presence or absence of integrin ligation provides specific information about the cellular microenvironment, and in many instances integrins serve as a conduit for signal transduction. Ligand binding by an integrin may promote its incorporation into focal adhesions, the assembly of cytoskeletal and intracellular signaling molecules into supra-molecular complexes, and the initiation of a cascade of downstream signaling events including protein phosphorylation, calcium release, and an increase in intracellular pH (reviewed by Schwartz et al. (1995) Ann. Rev. Cell Dev. Biol. 11:549–99). Such "outside-in" signaling ties into pathways controlling cell proliferation, migration and apoptosis (Stromblad et al. (1996) J. Clin. Invest. 98:426–33; Eliceiri et al. (1998) J. Cell. Biol. 140:1255–63). Integrins have been shown to play a role in such diverse physiological settings as embryonic development, wound healing, angiogenesis, clot formation, leukocyte extravasation, bone resorption and tumor metastasis.

The $\beta_3$-containing integrins are among the best studied of the receptor superfamily. The $\beta_3$ subunit forms heterodimers with either $\alpha_v$ ($\alpha_v\beta_3$) or $\alpha_{IIb}$ ($\alpha_{IIb}\beta_3$). While these integrins show substantial overlap in ligand specificity, they play very different roles in normal physiology and in disease.

$\alpha_v\beta_3$ is expressed by activated endothelial cells, smooth muscle cells, osteoclasts, and, at a very low level, by platelets. It is also expressed by a variety of tumor cell types. The integrin binds to a number of plasma proteins or proteins of the extracellular matrix, many of which are associated with sites of inflammation or wound healing (Albelda (1991) Am. J. Resp. Cell Mol. Biol. 4:195–203). These include vitronectin, fibronectin, osteopontin, von Willebrand factor, thrombospondin, fibrinogen, and denatured collagen Type I (Hynes (1992) Cell 69:11–25). Each of these proteins share a common sequence motif, arginine-glycine-aspartic acid (RGD), that forms the core of the integrin binding site.

$\alpha_v\beta_3$ has been most intensely studied in the context of new blood vessel formation (angiogenesis) where it mediates the adhesion and migration of endothelial cells through the extracellular matrix. Angiogenesis in adults is normally associated with the cyclical development of the corpus luteum and endometrium and with the formation of granulation tissue during wound repair. In the latter case, microvascular endothelial cells form vascular sprouts that penetrate into the temporary matrix within a wound. These cells transiently express $\alpha_v\beta_3$ and inhibition of the ligand binding function of the integrin temporarily inhibits the formation of granulation tissue (Clark et al. (1996) Am. J. Pathol. 148:1407–21). In cytokine-stimulated or unstimulated angiogenesis on the chick chorioallantoic membrane, blockade of $\alpha_v\beta_3$ with a heterodimer-specific antibody prevents new vessel formation without affecting the pre-existing vasculature (Brooks et al. (1994) Science 264:569–71). Furthermore, the loss of adhesive contacts by endothelial cells activated for angiogenesis induces a phenotype characteristic of apoptotic cells (Brooks et al. (1994) Cell 79:1157–64); that is, ligand binding by $\alpha_v\beta_3$ appears to transmit a survival signal to the cell. Thus, adhesion and/or signaling mediated by $\alpha_v\beta_3$ is essential for the formation of new blood vessels.

Solid tumors are unable to grow to significant size without an independent blood supply. It is currently hypothesized that the acquisition of an angiogenic phenotype is one of the limiting steps in the growth of primary tumors and of tumors at secondary sites (Folkman (1995) Nat. Med. 1:27–31). In addition, while the vasculature that penetrates a tumor mass provides a source of oxygen and nutrients, it also serves as a conduit for metastatic cells to leave the primary tumor and migrate throughout the body. Thus, inhibition of angiogenesis may limit both the growth and metastasis of cancerous lesions. In experimental settings of tumor-induced angiogenesis, inhibition of ligand-binding by endothelial $\alpha_v\beta_3$ prevented the formation of new blood vessels (Brooks et al. (1994) Cell 79:1157–64; Brooks et al. (1995) J. Clin. Invest. 96:1815–22), and inhibitors of $\alpha_v\beta_3$ were shown to reduce the growth of experimental tumors in vivo (Brooks et al. (1995) J. Clin. Invest. 96:1815–22; Carron et al. (1998) Canc. Res. 58:1930–5).

$\alpha_v\beta_3$ is not only expressed by the microvasculature within tumors, but in some cases, is also found on the surface of tumor cells themselves. In particular, expression of $\alpha_v\beta_3$ integrin has been detected in tissue sections from tumors of melanocytic and astroglial origin (Albelda et al. (1990) Canc. Res. 50:6757–64; Gladson and Cheresh (1991) J. Clin. Invest. 88:1924–32), and the level of integrin expression has been correlated with the stage or metastatic potential of the tumor (Albeldaet al. (1990) Canc. Res. 50:6757–64; Gladson et al. (1996) Am. J. Pathol. 148:1423–34; Hieken et al. (1996) J. Surg. Res. 63:169–73). Furthermore, melanoma cells grown in vitro in a three-dimensional matrix of denatured collagen undergo apoptosis upon $\alpha_v\beta_3$ blockade.

Data such as these have driven an interest in inhibitors of $\alpha_v\beta_3$ for the treatment of cancer. At present, two such inhibitors are in or near clinical trial: Vitaxin is a chimeric Fab fragment derived from the $\alpha_v\beta_3$-specific monoclonal antibody, LM609 (Wu et al. (1998) Proc. Nat. Acad. Sci. 95:6037–42). A phase I trial in late-stage cancer patients has been completed and no significant treatment-associated toxicities were observed (Gutheil et al. (1998) Am. Soc. Clin. Onc.). EMD121974 is a cyclic pentapeptide inhibitor of $\alpha_v\beta_3$. A Phase I study of this compound in Kaposi's sarcoma, brain tumors and solid tumors is scheduled to begin in 1999.

Angiogenesis (and $\alpha_v\beta_3$) are implicated in the pathology of several other diseases, including psoriasis (Creamer et al. (1995) Am. J. Pathol. 147:1661–7), rheumatoid arthritis (Walsh et al. (1998) Am. J. Pathol. 152:691–702; Storgard et al. (1999) J. Clin. Invest. 103:47–54), endometriosis (Healy et al. (1998) Hum. Reprod. Update 4:736–40), and several proliferative diseases of the eye (Casaroli Marano et al. (1995) Exp. Eye Res. 60:5–17; Friedlander et al. (1996) Proc. Nat. Acad. Sci. 93:9764–9; Hammes et al. (1996) Nat. Med. 2:529–33). Inhibition of integrin ligand binding in each of these contexts may provide significant therapeutic benefit.

Atheromatous plaque and restenosis following angioplasty are pathologies characterized by thickening of the intima, the innermost layer of the arterial wall. The proliferation and/or migration of smooth muscle cells into the neointima with concomitant deposition of fibrous extracellular proteins contributes to vessel wall thickening and subsequent vessel occlusion. Platelets may also contribute to the development of restenotic lesions through adhesion to endothelial cells and the release of growth factors and cytokines that stimulate the underlying smooth muscle cell layer (Le Breton et al. (1996) J. Am. Coll. Cardiol. 28:1643–51). $\alpha_v\beta_3$ integrin is expressed on arterial smooth muscle cells (Hoshiga et al. (1995) Circ. Res. 77:1129–35) and mediates their migration on vitronectin and osteopontin (Brown et al. (1994) Cardiovasc. Res. 28:1815–20; Jones et al. (1996) Proc. Nat. Acad. Sci. 93:2482–7; (Liaw et al. (1995) J. Clin. Invest. 95:713–24; Panda et al. (1997) Proc. Nat. Acad. Sci. 94:9308–13), both matrix proteins that are associated with atheroschlerotic tissues in vivo (Brown et al. (1994) Cardiovasc. Res. 28:1815–20; Giachelli et al. (1995) Ann. N. Y. Acad. Sci. 760:109–26; Pandaet al. (1997) Proc. Nat. Acad. Sci. 94:9308–13). In addition, $\alpha_v\beta_3$ expression on endothelial cells, and to a much lesser extent on platelets, is responsible for at least part of the adhesive interaction between these cell types (Le Breton et al. (1996) J. Am. Coll. Cardiol. 28:1643–51; Gawaz et al. (1997) Circulation 96:1809–18). $\alpha_v\beta_3$ blockade with RGD-containing peptides or a monoclonal antibody was found to limit neointimal hyperplasia in several animal models of restenosis following arterial injury (Choi et al. (1994) J. Vasc. Surg. 19:125–34; Srivatsa et al. (1997) Cardiovasc. Res. 36:408–28; Slepian et al. (1998) Circulation 97:1818–27; Coleman et al. (1999) Circ. Res. 84:1268–76). Furthermore, treatment of patients undergoing percutaneous coronary intervention with an anti-β3 antibody (Reopro/abciximab/c7E3), which blocks both the platelet fibrinogen receptor, $\alpha_{IIb}\beta_3$, and $\alpha_v\beta_3$ provided long term reduction in the rates of death or myocardial infarction and in the rate of reocclusion of the artery (Lefkovits et al. (1996) Am. J. Cardiol. 77:1045–51), an effect that may be mediated through inhibition of $\alpha_v\beta_3$ ligation. The observation that $\alpha_v\beta_3$ is expressed by microvascular smooth muscle cells after experimentally-induced focal cerebral ischemia (Okada et al. (1996) Am. J. Pathol. 149:37–44) suggests that this integrin may also play some role in the development of ischemia/reperfusion injury in stroke.

Finally, $\alpha_v\beta_3$ mediates the attachment of osteoclasts to matrix proteins, particularly osteopontin, on the surface of bone. Osteoclasts are responsible for the resorption of bone in normal physiology as well as in pathological conditions such as osteoporosis. A monoclonal antibody specific for $\alpha_v\beta_3$ inhibited the binding and resorption of bone particles by osteoclasts in vitro (Ross et al. (1993) J. Biol. Chem. 268:9901–7). Furthermore, an RGD-containing protein, echistatin, was shown to block parathyroid-stimulated bone resorption in an animal model, as monitored by serum calcium levels (Fisher et al. (1993) Endocrin. 132:1411–3). Inhibitors of $\alpha_v\beta_3$ integrin are thus considered of potential utility in treating debilitating bone loss such as occurs in osteoporosis.

$\alpha_{IIb}\beta_3$ (also referred to as GPIIbIIIa) is the major integrin on the surface of platelets where it mediates the adhesion of activated platelets to the plasma protein fibrinogen (Nachman and Leung (1982) J. Clin. Invest. 69:263–9; Shattil et al. (1985) J. Biol. Chem. 260:11107–14). During clot formation, fibrinogen dimers cross-link platelets to one another through the integrin receptor. $\alpha_{IIb}\beta_3$ also binds to several other plasma and cell matrix proteins, including von Willebrand factor, vitronectin, and fibronectin (Faull and Ginsberg (1996) J. Am. Soc. Nephrol. 7:1091–7).

Clot formation is a tightly regulated process that balances the need for rapid response to vascular injury with the risk of aberrant occlusion of critical vessels. The $\alpha_{IIb}\beta_3$ heterodimer is constitutively expressed on the surface of resting platelets at approximately 80,000 copies per cell (Wagner et al. (1996) Blood 88:907–14); however, the affinity of the integrin for fibrinogen is very low on these cells. Activation of platelets by ADP, epinephrine, collagen or thrombin leads to a dramatic enhancement in integrin ligand binding activity (Bennett and Vilaire (1979) J. Clin. Invest. 64:1393–401; Marguerie et al. (1979) J. Biol. Chem. 254:5357–63), probably accomplished through a conformational change in the receptor (Shattil et al. (1985) J. Biol. Chem. 260:11107–14; O'Toole et al. (1990) Cell Reg. 1:883–93; Du et al. (1993) J. Biol. Chem. 268:23087–92). In this prototypic example of "inside-out" control of integrin function, cross-linking of platelets through the $\alpha_{IIb}\beta_3$-fibrinogen interaction is confined to local sites of platelet activation.

Inhibitors of $\alpha_{IIb}\beta_3$ ligand binding have been primarily explored in the context of cardiovascular disease (Chong (1998) Am. J. Health Syst. Pharm. 55:2363–86; Topol et al. (1999) Lancet 353:227–31), but may have application in any of a number of indications where thrombus formation is suspected or is likely. Three $\alpha_{IIb}\beta_3$ inhibitors have been approved for use in patients experiencing acute coronary syndrome and/or in patients who are undergoing percutaneous coronary intervention. Reopro (Centocor/Eli Lilly) is a humanized murine monoclonal antibody Fab fragment with specificity for the $\beta_3$ chain of $\alpha_{IIb}\beta_3$. Integrilin (COR Therapeutics) is a cyclic heptapeptide based on the integrin binding site of barbourin, an $\alpha_{IIb}\beta_3$ inhibitory protein derived from snake venom. Aggrastat (Merck & Co.) is a non-peptide small molecule antagonist of the integrin. Unlike the small molecule inhibitors, Reopro cross-reacts with $\alpha_v\beta_3$ a fact which may account for the greater reduction in long-term rates of death and non-fatal myocardial infarction associated with its use (see above). A significant effort is underway to identify new inhibitors of the platelet integrin with characteristics not found in the cohort of approved drugs. Specifically, compounds with specificity for the active, ligand-binding conformation of $\alpha_{IIb}\beta_3$ may reduce the risk of bleeding complications associated with the existing anti-clotting therapies. Orally available compounds would be particularly useful for longer term therapy of patients at risk for recurrent myocardial infarction or unstable angina.

Given the role of integrins in the various disease states described above, it would be desirable to have high specificity inhibitors of particular integrins. The present invention provides such agents.

The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands" and, U.S. Pat. No. 5,270,163 (see also WO 91/19813) entitled Methods for Identifying "Nucleic Acid Ligands," each of which is specifically incorporated by reference herein. Each of these applications, collectively referred to herein as the SELEX Patent Applications, describes a fundamentally novel method for making a nucleic acid ligand to any desired target molecule. The SELEX process provides a class of products which are referred to as nucleic acid ligands or aptamers, each having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands,", now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8, 1998, entitled "Systematic Evolution of Ligands by Exponential Enrichment: Photoselection of Nucleic Acid Ligands and Solution SELEX" describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, which can be non-peptidic, termed Counter-SELEX. U.S. Pat. No. 5,567,588 entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel Modified Nucleosides by Intramolecular Nucleophilic Displacement, now abandoned," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by EXponential Enrichment: Chimeric SELEX," and U.S. Pat. No. 5,683,867 entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled "Nucleic Acid Ligand Complexes". Each of the above described patent applications which describe modifications of the basic SELEX procedure are specifically incorporated by reference herein in their entirety.

It is an object of the present invention to provide methods that can be used to identify nucleic acid ligands that bind with high specificity and affinity to particular integrins.

It is a further object of the present invention to obtain nucleic acid ligands to particular integrins that inhibit the ability of that integrin to bind its cognate ligand.

It is a further object of the present invention to obtain integrin inhibiting pharmaceutical compositions for controlling thrombosis, tumor angiogenesis, tumor cell migration, proliferative ocular diseases, rheumatoid arthritis, psoriasis, osteoporosis, and restenosis.

It is yet a further object of the invention to obtain imaging agents for the non-invasive detection of deep vein or arterial thrombi.

SUMMARY OF THE INVENTION

Methods are provided for generating nucleic acid ligands to integrins, particularly to the $\beta_3$ integrins. The methods use the SELEX process for ligand generation. Particular embodiments describe the isolation of nucleic acid ligand inhibitors of both $\alpha_v\beta_3$ and $\alpha_{IIb}\beta_3$. The nucleic acid ligand inhibitors are derived from a library of 2'-fluoro-pyrimidine RNA sequences and were selected for high affinity binding to $\alpha_v\beta_3$. One of the modified nucleic acid ligands is shown to inhibit the binding of either vitronectin or fibrinogen to both of the purified integrins in vitro. This nucleic acid ligand binds to the surface of both resting and activated platelets with equivalent affinity and accumulates at the site of a preformed clot in an animal model of venous thrombosis.

The nucleic acid ligands provided by the invention are useful as therapeutic agents for a number of diseases including thrombosis and cancer. The nucleic acid ligands of the instant invention are also useful as diagnostic agents for thrombosis.

BRIEF DESCRIPTION OF THE DRAWINGS

FIG. 1 illustrates the binding of affinity-enriched RNA pools to immobilized $\alpha_v\beta_3$. 5'-biotinylated RNA pools were incubated at varying concentrations in 96-well microtiter plates coated with integrin $\alpha_v\beta_3$. Bound RNAs were detected via the biotin moiety by a chromogenic assay. Data are expressed in absorbance units at 405 nm as a function of input RNA concentration.

FIG. 2 illustrates cross-reactivity of aptamer 17.16 to purified integrin $\alpha_{IIb}\beta_3$. 5'-biotinylated aptamer 17.16 (SEQ ID NO:60) was incubated at varying concentrations in microtiter wells coated with either integrin $\alpha_v\beta_3$ or $\alpha_{IIb}\beta_3$. Bound RNA was detected via the biotin moiety using a chromogenic assay. Data are expressed as the per cent of the maximum signal to normalize for differences in protein coating.

FIG. 3 illustrates cross-reactivity of aptamer 17.16 (SEQ ID NO: 60) to purified integrin $\alpha_v\beta_5$. 5'-biotinylated aptamer 17.16 or a control RNA of similar length and base composition were incubated at varying concentrations in microtiter wells coated with either $\alpha_v\beta_3$ or $\alpha_v\beta_5$. Bound RNAs were detected via the biotin moiety by a chromogenic assay. Data are expressed in absorbance units at 405 nm as a function of input RNA concentration.

FIGS. 4A–D illustrates $\beta_3$ aptamer inhibition of integrin ligand binding. Biotinylated fibrinogen or vitronectin were incubated in microtiter wells coated with either integrin $\alpha_v\beta_3$ or $\alpha_{IIb}\beta_3$ in the presence or absence of varying concentrations of ligand binding competitors. Competitors included aptamer 17.16 (SEQ ID NO: 60), a control RNA of similar length and base composition, a cyclic RGD peptide (cRGD, see Materials and Methods), an $\alpha_v\beta_3$-specific monoclonal antibody (LM609), or unmodified fibrinogen or vitronectin. Bound ligands were detected via biotin using a chromogenic assay. Data are expressed in absorbance units at 405 nm as a function of input competitor concentration. FIG. 4A illustrates FIG. 4A shows competition of vitronectin binding to immobilized $\alpha_v\beta_3$; FIG. 4B shows competition of fibrinogen binding to immobilized $\alpha_v\beta_3$; FIG. 4C shows competition of fibrinogen binding to immobilized $\alpha_{IIb}\beta_3$. An estimate of the maximum absorbance value was determined for each ligand/integrin pair in the absence of competitor. The baseline absorbance value was determined by adding 5 mM EDTA to the incubation buffer. The maximum and minimum values so determined were FIG. 4A, 0.914/0.113; FIG. 4B, 1.042/0.122; FIG. 4C, 0.889/0.128.

FIG. 5 illustrates binding of aptamer 17.16 (SEQ ID NO: 60) to activated or resting human platelets. 5'-fluorescein-conjugated aptamer 17.16 or a control RNA of similar length and base composition were incubated at various concentrations with resting or thrombin-activated human platelets ($10^6$/ml). Incubations were at room temperature in buffered saline containing divalent cations, 0.1% BSA and 0.01% NaAzide. Mean fluorescence intensity of the sample was determined by flow cytometry both before and after the addition of EDTA to 5 mM final concentration. The difference in fluorescence intensity between the two samples (the EDTA-sensitive signal) is shown as a function of the concentration of aptamer or control RNA.

FIG. 6 illustrates biodistribution of [$^{99m}$Tc]-aptamer 17.16 or control RNA in a rabbit venous clot model. A clot derived from human platelet-rich plasma was generated in situ by temporary isolation of the jugular vein of an anesthetized rabbit. After restoration of circulation over the clot, [$^{99m}$Tc]-labeled aptamer or control RNA were injected into the bloodstream of the rabbit via the ipsilateral ear vein. After one hour, the animal was sacrificed and tissues were weighed and counted in a gamma counter. Accumulation of radioactivity in various tissues is reported as the percentage of the injected dose per gram wet weight of tissue.

DETAILED DESCRIPTION OF THE PREFERRED EMBODIMENTS

Figure 4A:
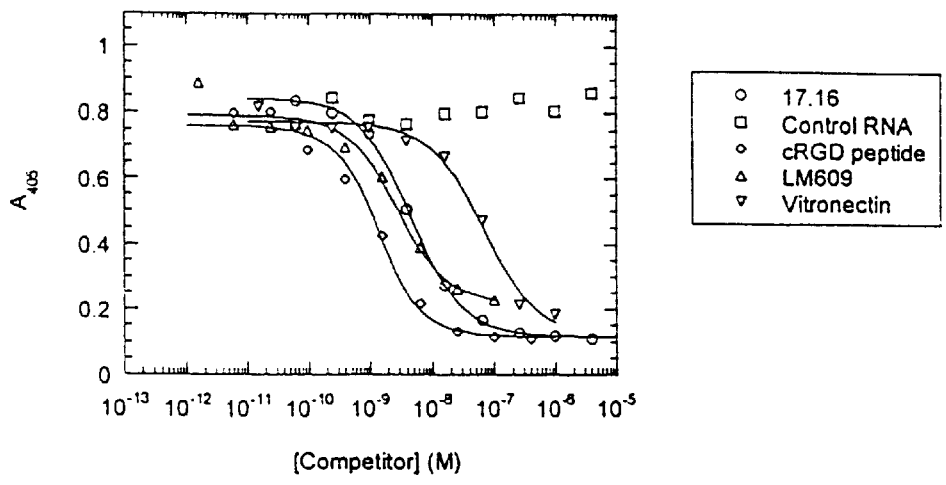

The central method utilized herein for identifying nucleic acid ligands to Integrins is called the SELEX process, an acronym for Systematic Evolution of Ligands by Exponential enrichment and involves (a) contacting the candidate mixture of nucleic acids with integrins, or expressed domains or peptides corresponding to integrins, (b) partitioning between members of said candidate mixture on the basis of affinity to integrins, and c) amplifying the selected molecules to yield a mixture of nucleic acids enriched for nucleic acid sequences with a relatively higher affinity for binding to integrins.

Definitions

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target. Nucleic acid ligands are often referred to as "aptamers". The term aptamer is used interchangeably with nucleic acid ligand throughout this application. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In the present invention, the target is an integrin, or portions thereof. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to integrins.

The SELEX methodology is described in the SELEX Patent Applications.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX targets are integrins.

As used herein, "solid support" is defined as any surface to which molecules may be attached through either covalent or non-covalent bonds. This includes, but is not limited to, membranes, microtiter plates, magnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces.

Note that throughout this application, various references are cited. Every reference cited herein is specifically incorporated in its entirety.

A. Preparing Nucleic Acid Ligands to Integrins.

In the preferred embodiment, the nucleic acid ligands of the present invention are derived from the SELEX methodology. The SELEX process is described in U.S. patent application Ser. No. 07/536,428, entitled Systematic Evolution of Ligands by Exponential Enrichment, now abandoned, U.S. Pat. No. 5,475,096 entitled nucleic acid ligands and U.S. Pat. No. 5,270,163 (see also WO 91/19813) entitled methods for identifying nucleic acid ligands. These applications, each specifically incorporated herein by reference, are collectively called the SELEX Patent Applications.

The SELEX process provides a class of products which are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. patent application Ser. No. 07/960,093, filed Oct. 14, 1992, now abandoned, and U.S. Pat. No. 5,707,796 both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8, 1998, entitled "Systematic Evolution of Nucleic Acid Ligands by Exponential Enrichment: Photoselection of Nucleic Acid Ligands and Solution SELEX" all describe a SELEX based method for selecting nucleic acid ligands containing photoreactive groups capable of binding and/or photo crosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588 entitled "Systematic Evolution of Ligands by Exponential Enrichment: Solution SELEX," describes a SELEX-based method which achieves highly efficient partitioning between oligonucleotides having high and low affinity for a target molecule. U.S. Pat. No. 5,496, 938 entitled "Nucleic Acid Ligands to HIV-RT and HIV-1 Rev," describes methods for obtaining improved nucleic acid ligands after SELEX has been performed. U.S. Pat. No. 5,705,337 entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by Exponential Enrichment: Chimeric SELEX," and U.S. Pat. No. 5,683,867 entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

In U.S. Pat. No. 5,496,938 methods are described for obtaining improved nucleic acid ligands after the SELEX process has been performed. This patent, entitled Nucleic Acid Ligands to HIV-RT and HIV-I Rev, is specifically incorporated herein by reference.

One potential problem encountered in the diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 8, 1993, now abandoned, and U.S. Pat. No. 5,660,985, both entitled "High Affinity Nucleic Acid Ligands Containing Modified Nucleotides", and the U.S. Patent Application entitled "Transcription-free SELEX", U.S. application Ser. No. 09/356,578, filed Jul. 28, 1999, each of which is specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3'and 5'modifications such as capping. In preferred embodiments of the instant invention, the nucleic acid ligands are RNA molecules that are 2'-fluoro (2'-F) modified on the sugar moiety of pyrimidine residues.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

The nucleic acid ligands of the invention are prepared through the SELEX methodology that is outlined above and thoroughly enabled in the SELEX applications incorporated herein by reference in their entirety. The SELEX process can be performed using purified integrins, or fragments thereof as a target. Alternatively, full-length integrins, or discrete domains of integrins, can be produced in a suitable expression system. Alternatively, the SELEX process can be performed using as a target a synthetic peptide that includes sequences found in an integrin. Determination of the precise number of amino acids needed for the optimal nucleic acid ligand is routine experimentation for skilled artisans.

In some embodiments, the nucleic acid ligands become covalently attached to their targets upon irradiation of the nucleic acid ligand with light having a selected wavelength. Methods for obtaining such nucleic acid ligands are detailed in U.S. patent application Ser. No. 08/123,935, filed Sep. 17, 1993, entitled "Photoselection of Nucleic Acid Ligands," now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8 1998, entitled "Systematic Evolution of Ligands by Exponential Enrichment: Photoselection of Nucleic Acid Ligands and Solution SELEX" each of which is specifically incorporated herein by reference in its entirety.

In preferred embodiments, the SELEX process is carried out using integrins attached to polystrene beads. A candidate mixture of single stranded RNA molecules is then contacted with the beads. In especially preferred embodiments, the single stranded RNA molecules have a 2'-fluoro modification on C and U residues, rather than a 2'-OH group. After incubation for a predetermined time at a selected temperature, the beads are washed to remove unbound candidate nucleic acid ligand. The nucleic acid ligand that binds to the integrin is then released into solution, then reverse transcribed by reverse transcriptase and amplified using the Polymerase Chain Reaction. The amplified candidate mixture is then used to begin the next round of the SELEX process. Example 2 illustrates one possible way of performing the SELEX process using integrins as targets.

In preferred embodiments, the nucleic acid ligands thus obtained are assayed for their ability to inhibit the interaction of the integrin with its cognate ligand. In one embodiment, this is performed by first coating microtiter plates with the appropriate integrin(s). A ligand for the integrin, such as vitronectin or fibrinogen, is then biotinylated and contacted with the coated integrin in the presence of the nucleic acid ligand to be assayed. After incubation for a suitable period of time, the microtiter plate is washed, and the amount of vitronectin or fibrinogen binding to integrin is quantitated by adding a streptavidin-alkaline phosphatase conjugate, followed by a colorimetric substrate for alkaline phosphatase, such as p-nitrophenyl phosphate. The alkaline phosphatase signal in each well of the plate is thus inversely proportional to the effectiveness of the nucleic acid ligand as an inhibitor of the interaction between the bound integrin and its cognate ligand.

In other embodiments, the nucleic acid ligands can be analyzed using binding to human platelets as an assay. This can be done, for example, by fluorescently labelling the nucleic acid ligand by any of the numerous techniques known in the art. The fluorescent nucleic acid ligand can then be contacted with platelets, and the amount of nucleic acid ligand can be quantitated using Fluorescence Activated Cell Sorting (FACS).

The distribution of the nucleic acid ligands of the instant invention can also be studied in vivo. In some embodiments, nucleic acid ligands are labelled with a radiolabel used in the art of radioimaging. For example, a nucleic acid ligand can be conjugated to the isotope $^{99m}Tc$ using one of a number of techniques known in the art. The radiolabelled nucleic acid can then be studied in an animal model of venous thrombosis. For example, a human blood clot can be generated in rabbit vein by first isolating the vein in situ by ligation, and then infusing the vein with human platelet-rich plasma and heparin to induce the formation of a blood clot. Blood flow through the vein is then re-established, and the radiolabelled nucleic acid ligand is introduced into the animals blood supply. The distribution of the radiolabelled nucleic acid ligand can then be studied in the rabbit's tissues to determine whether the nucleic acid ligand has accumulated in the clot, rather than in other areas.

The nucleic acid ligands provided by the instant invention have a number of potential uses as therapeutic and diagnostic agents. In some embodiments, nucleic acid ligands that inhibit the interaction between platelet-expressed integrins and their cognate ligands are administered, along with pharmaceutically accepted excipients, in order to prevent the formation of blood clots in patients susceptible to deep vein thrombosis. In other embodiments, the nucleic acid ligands are used to treat acute thrombosis formation during and following percutaneous coronary intervention. In still other embodiments, the nucleic acid ligands of the invention are used to treat patients with acute coronary syndromes such as unstable angina or myocardial infarction.

In other embodiments, radiolabelled nucleic acid ligands to platelet-expressed integrins are administered to individuals who are to undergo major surgery, or have suffered major trauma. Such nucleic acid ligands can function as imaging agents for the detection of thrombi, by showing sites in the body where large aggregations of platelets are present. If a thrombosis is detected by radioimaging at a critical site in the body, then anticoagulant and thrombolytic treatment—including treatment with the inhibitory nucleic acid ligands of the instant invention—can be given locally. The advantage of using such a nucleic acid ligand imaging agent is that the anticoagulant and thrombolytic treatments—which can cause harm if administered prophylactically by allowing internal bleeding to continue without efficient clotting—can be given only to those individuals who definitely have a dangerous thrombosis. Moreover, these treatments can be specifically injected at the site where the thrombosis has been detected by the nucleic acid ligand, instead of injecting higher concentrations into the bloodstream in the hope that some active agent will be carried to all potential sites of thrombosis.

Nucleic acid ligands to $\alpha_v\beta_3$ integrin can be used to inhibit tumor growth and metastasis. They can also be used to treat ocular diseases including, but not limited to, diabetic retinopathy, retinopathy of prematurity, and macular degeneration. Other diseases for which $\alpha_v\beta_3$ nucleic acid ligands are useful therapeutic agents include, but are not limited to, endometriosis, psoriasis, rheumatoid arthritis, stroke, osteoporosis, and restenosis.

EXAMPLES

The following examples are given for illustrative purposes only. They are not to be taken as limiting the scope of the invention in any way.

Example 1

Isolation of Integrins and Integrin Ligands $\alpha_v\beta_3$ integrin was isolated from human placenta and purified by immunoaffinity chromatography essentially as described by (Smith and Cheresh (1988) J. Biol. Chem. 263:18726–31). In brief, human placentas were diced and the tissue fragments were extracted in a buffer containing 100 mM octyl-β-D-glucopyranoside detergent (Calbiochem, San Diego, Calif.). The extract was cleared by centrifugation and applied to an immunoaffinity column $\alpha_v\beta_3$-specific monoclonal antibody LM609 affixed to Affi-Gel 10, (Chemicon International, Inc., Temecula, Calif.)). Protein bound to the column was eluted with a low-pH buffer and fractions were immediately neutralized and analyzed for integrin content by SDS-polyacrylamide gel electrophoresis. Integrin-containing fractions were pooled and aliquots of the purified material were stored at −80° C. Purified human $\alpha_v\beta_3$ was also purchased from Chemicon International, Inc, as was human $\alpha_v\beta_5$ integrin $\alpha_{IIb}\beta_3$ and fibrinogen were purchased from Enzyme Research Laboratories, Inc. (South Bend, Ind.). Vitronectin was purified from outdated human plasma according to the procedure of (Yatohgo et al. (1988) Cell Struct. Func. 13:281–92), using heparin affinity chromatography.

Example 2

Generating Nucleic Acid Ligands to Integrins Using the SELEX Method A DNA Template Library of Sequence:

| 5'-ttatacgactcactatagggagacaa-gaataaacgctcaannnnnnnnnnnnnnnnnnnnnnnnnnnnnnnnnnnnnnttcgacaggaggctcacaacaggc-3' | SEQ ID NO:1 | was prepared by chemical synthesis. The italicized nucleotides correspond to a T7 RNA polymerase promoter. There are 40 n residues (a,g,t, or c). A short DNA primer "3N8":

| 5'-gcctgttgtgagcctcctgtcgaa-3' | SEQ ID NO:2 | was annealed to the template and extended using Klenow DNA polymerase (New England Biolabs, Beverly, Mass.). The double-stranded DNA product served as a product for T7 RNA polymerase transcription (enzyme obtained from Enzyco, Inc., Denver, Colo.) to generate a library of random-sequence RNAs. 2'-fluoro-CTP and -UTP were used in place of the 2'-OH-pyrimidines.

For application of the SELEX process to $\alpha_v\beta_3$ integrin, the purified protein was diluted 1000-fold from detergent-containing storage buffer into 50 mM MES (2-[N-morpholino]ethanesulfonic acid), pH 6.1, 150 mM NaCl, 2 mM $CaCl_2$, to a final concentration of approximately 0.2 μg/ml. 3.2 μpolystyrene particles (IDEXX Laboratories, Inc., Westbrook, Me.) were added to the diluted protein and the mixture was rotated overnight at 4° C. The beads were collected by centrifugation and blocked by incubation in 3% BSA in MES buffer (above) for one hour at room temperature. Blocked beads were washed several times by resuspension in binding buffer (50 mM Tris.HCl, pH 7.4 (at 37° C.), 145 mM NaCl, 4 mM KCl, 1 mM $MgCl_2$, 2 mM $CaCl_2$, 0.1 mM $MnCl_2$, 0.01% BSA). For one round of selection, integrin-coated beads were mixed with RNA and rotated at 37° C. for 4 hours to allow equilibration of the RNA with the immobilized protein. The beads were then collected by centrifugation and washed at least 5 times in binding buffer by rapid resuspension and pelleting, without additional incubation. RNAs that remained bound to the beads were eluted overnight at 37° C. in binding buffer plus 100 μM cyclic RGD peptide ("cRGD") (GPenGRGDSPCA, Life Technologies, Gibco BRL, Gaithersburg, Md.). Eluted RNAs were extracted with phenol, then chloroform:isoamyl alcohol (24:1), and ethanol precipitated. The RNA pellet was resuspended and annealed to primer 3N8 for reverse transcription using avian myeloblastosis virus reverse transcriptase (Life Sciences, Inc., St. Petersburg, Fla.). The cDNA pool was amplified by the polymerase chain reaction using the 3N8 primer and primer "5N8":

| 5'-taatacgactcactatagggagacaagaataaacgctcaa-3' | SEQ ID NO:3 | and T. aquaticus DNA polymerase (Perkin Elmer-Cetus, Foster City, Calif.). Transcription of the PCR product generated an RNA pool to initiate a new round of selection. For the first round of selection 1 nmol of RNA (approximately $6 \times 10^{14}$ sequences) was incubated at 2 μM concentration with a volume of bead suspension equivalent to 50 pmol of protein (assuming all the integrin had adsorbed to the beads). In subsequent rounds, the concentration of RNA and protein-coated beads were both reduced to demand higher affinity binding interactions.

The affinity of individual RNAs and RNA pools for $\alpha_v\beta_3$ was determined by titration of biotinylated RNA with a small quantity of immobilized integrin. Bound RNA was detected through the biotin moiety. Biotinylated RNA was prepared according to standard transcription protocols, but including a 5-fold molar excess of a 5'-biotin-modified GMP over GTP in the reaction mixture. Methods for synthesizing 5'-biotin-modified guanosine nucleotides are described in WO 98/30720 entitled "Bioconjugation of Oligonucleotides", specifically incorporated herein by reference in its entirety. The modified nucleotide is incorporated at the 5' end of the transcript in proportion to its representation in the guanosine pool. 96-well microtiter plates (Immulon 2, Dynatech Laboratories, Inc., Chantilly, Va.) were coated overnight at 4° C. with 100 μl purified $\alpha_v\beta_3$ at a concentration of 0.25 μg/ml in 20 mM Tris.HCl, pH 7.5, 150 mM NaCl, 1 mM $MgCl_2$, 2 mM $CaCl_2$, 0.1 mM $MnCl_2$. Coating concentrations were 0.8 μg/ml for $\alpha_{IIb}\beta_3$ and 0.3 μg/ml for $\alpha_v\beta_5$. Wells were blocked with 200 μl of a solution of 3% BSA in the same buffer (1 hour at room temperature) then rinsed 3 times with 200 μl binding buffer (50 mM Tris.HCl, pH 7.5, 137 mM NaCl, 2.7 mM KCl, 1 mM $MgCl_2$, 2 mM $CaCl_2$, 0.1 mM $MnCl_2$, 0.1% BSA). Individual RNAs or RNA pools were denatured briefly at 93° C. in binding buffer without divalent cations or BSA, then serially diluted in the same buffer. 50 μl binding buffer containing 2×-concentrations of divalent cations and BSA were added to each well, followed by 50 μl RNA dilution. RNAs were allowed to incubate in the integrin-coated wells at 37° C. for 30–60 minutes. Unbound RNAs were removed by 3 rapid washes in binding buffer. To detect bound RNA, 100 μl of a 1:2500 dilution in binding buffer of streptavidin-alkaline phosphatase conjugate (Calbiochem) were incubated in each well for 30 minutes at room temperature, followed by three rapid washes, as above. 100 μl/well p-nitrophenyl phosphate (Sigma Chemical Co., St. Louis, Mo.) was added and incubated at room temperature for 30 minutes. Color development was monitored by absorbance at 405 rm. Binding data were fit to an equation that describes the fraction of RNA or protein bound as a function of $K_D$, and the total concentrations of RNA and protein in the binding reaction for both monophasic and biphasic binding behavior (Green et al. (1996) Biochem. 35:14413–24). A control RNA corresponding to a sequence-scrambled version of aptamer 7.24:

> 5'-gggagacaagaauaaucgcucaacg-
> uugaaugcugcauuauggaguauugaccgcuacauccccuucgaca ggaggcu-
> cacaacaggc-3'                                              SEQ ID NO:4 was used to monitor non-specific binding of RNA under the conditions of the assay.

After seven rounds of the SELEX process, the amount of RNA specifically bound to the integrin-coated beads had increased substantially (data not shown). Although immobilized $\alpha_v\beta_3$ showed no detectable affinity for random sequence RNA, the Round 7 RNA pool bound with an equilibrium dissociation constant ($K_D$) of approximately $4\times10^{-7}$ M (FIG. 1). The Round 7 affinity-enriched pool was cloned and sequences were determined for individual molecules in the mixture. Of 92 sequences obtained, 35 (38%) were very highly related to one another, in many cases differing at no more than a single base position. These sequences are collectively referred to as "Family 1." It is likely that many if not most of these RNAs derived from a single precursor as a result of errors in replication during the RT and PCR steps. Another 25 sequences (27%) shared a short motif (CCUGCC) that defined a second sequence family ("Family 2"). The remaining 32 sequences (35%) were not obviously related to sequences in Families 1 or 2 and were thus termed "orphan" sequences. The large percentage of orphan sequences in the round 7 pool suggested that a great deal of sequence complexity remained in the population. Therefore, the SELEX process was continued in the hope of further enriching for high affinity sequences whose representation in the round 7 pool may have been low. Indeed, a substantial improvement in the affinity of the RNA pool was observed after 8 additional rounds of affinity selection (Round 15, FIG. 1). No further improvement was seen after two more rounds of selection (Round 17, FIG. 1), so clones were isolated from the Round 15 and Round 17 RNA pools and the sequences of individual isolates were compared to those obtained at Round 7. Twenty-seven of 39 sequences derived from the Round 15 pool (69%) were members of the highly conserved sequence family, Family 1. Three sequences (8%) could be grouped with Family 2 and 9 sequences (23%) were orphans. All of the 18 sequences isolated from the Round 17 pool were members of sequence Family 1. Thus, in this case, additional rounds of the SELEX process served to focus the RNA population on a single high-affinity sequence family that was already predominate at Round 7.

Table 1 shows the sequences of the major family of 2'-F-pyrimidine RNAs with high affinity for $\alpha_v\beta_3$ (Family 1). Clone names indicate the selected RNA pool from which each sequence was derived (round 7, round 15 or round 17) followed by a unique clone number. Note that in several cases identical sequences were isolated from different RNA pools; in these cases, both clone names are given. (Clones 17.12A and B were isolated as end-to-end inserts in a single plasmid.) Numbers in parentheses indicate the frequency with which a particular sequence was isolated; if no number is given the clone was obtained only once from the selected RNA pool. Sequences of the 5' and 3' fixed sequence regions common to all of the clones are shown at the top in lower case letters. Gaps have been inserted into many of the sequences to highlight the strong sequence conservation among most of the clones. The length of the random sequence region is shown for each RNA, as well as an estimate of the $K_D$ for binding to immobilized $\alpha_v\beta_3$, where it was determined (ND=not determined). The $K_D$ value provided is generally based on one or the average of two determinations. Family 2 sequences isolated from the $\alpha_v\beta_3$ SELEX are shown in Table 2. The short motif (CCUGCC) held in common among all the sequences is indicated in boldface letters. In Table 3, sequences with no obvious relationship to Families 1 or 2 are shown. Groups of similar sequences with only two (7.41 and 7.93) or three (7.11, 7.82 and 7.101) members are also included in Table 3.

The substantial affinity improvement between rounds 7 and 15 must be due in part to the loss of lower affinity species from the population; however, the introduction of and selection for higher affinity sequence variants of Family 1 may also have contributed to the overall affinity enrichment of the pool. While the affinity of relatively few sequences from the Round 7 pool were measured, their affinities for immobilized $\alpha_v\beta_3$ were generally less than that of RNAs derived from Rounds 15 and 17 (Tables 1–3).

Example 3

Specificity of the Nucleic Acid Ligands to Integrins

In general, aptamers selected for high-affinity binding to a particular target protein show relatively weak binding to other related proteins, except in cases where the degree of homology is very high (for example, see (Green et al. (1996) Biochem. 35:14413–24; Ruckman et al. (1998) J. Biol. Chem. 273:20556–67)). Significant homology exists within the families of integrin alpha and beta sub-units, and both alpha and beta sub-units are shared among members of the integrin superfamily. Thus, it was of interest to assess the relative affinity of the $\alpha_v\beta_3$ aptamers for closely related integrins. The affinities were determined using the methods described above. The Family 1 aptamer, 17.16(SEQ ID NO: 60), was chosen as a representative of the major sequence family. FIG. 2 shows that aptamer 17.16 bound with identical affinity to purified, immobilized $\alpha_v\beta_3$ and to the platelet integrin, $\alpha_{IIb}\beta_3$ in a 96-well plate binding assay. Although these two proteins share the $\beta_3$ sub-unit in common, an alignment of the $\alpha_v$ and $\alpha_{IIB}$ amino acid sequences shows only 36% overall sequence identity (Fitzgerald et al. (1987) Biochem. 126:8158–65). Short stretches of exact sequence identity, 5 to 9 amino acids in length, do occur, primarily within four putative calcium-binding domains of each $\alpha$ sub-unit. Binding of aptamer 17.16 to integrin $\alpha_v\beta_5$ was also tested. The $\beta_5$ sub-unit shares 56% sequence identity with $\beta_3$ and is more closely related to $\beta_3$ than other members of the beta sub-unit family (McLean et al. (1990) J. Biol. Chem. 265:17126–31; Suzuki et al. (1990) Proc. Nat. Acad. Sci. 87:5354–8). No aptamer binding to immobilized integrin $\alpha_v\beta_5$ was observed (FIG. 3), although an $\alpha_v$-specific antibody detected the presence of $\alpha_v\beta_5$ protein adsorbed to the surface of the well (data not shown). Together, these data strongly suggest that aptamer 17.16, and by extension the other members of sequence Family 1, bind primarily to the $\beta_3$ sub-unit of $\alpha_v\beta_3$. Furthermore, the high-affinity binding of the aptamer to the platelet integrin, $\alpha_{IIb}\beta_3$ extends its range of potential application to indications involving detection of platelets or inhibition of their function.

Example 4

Aptamer Inhibition of Ligand Binding to Purified Integrins

While the SELEX process identifies RNA sequences with high affinity for a particular target, the procedure used in this example was designed to bias for the recovery of ligand binding site inhibitors by the inclusion of a cRGD peptide competitor in the elution buffer. To test whether aptamer 17.16 could block the ligand binding site of $\alpha_v\beta_3$ or $\alpha_{IIb}\beta_3$, purified vitronectin and fibrinogen were biotinylated and incubated with one or both of the immobilized integrins in the presence or absence of varying concentrations of the aptamer or a non-binding control RNA. This was done as follows: purified integrin ligands, vitronectin and fibrinogen, were biotinylated according to (Smith et al. (1990) J. Biol. Chem. 265:12267–71). Briefly, proteins were dialyzed into 0.1 M NaHCO$_3$, 0.1 M NaCl. N-hydroxysuccinimido-LC-biotin (Pierce) was dissolved at 1 mg/ml in DMSO and added to the protein at a ratio of 0.1 mg biotin per 1 mg protein. The reaction was allowed to rotate at room temperature for 2 hours. Biotinylated proteins were dialyzed into phosphate-buffered saline and their concentrations determined by absorbance at 280 nm. 96-well microtiter plates were coated as described above with either $\alpha_v\beta_3$ or $\alpha_{IIb}\beta_3$ and blocked with BSA. A fixed concentration of biotinylated ligand (fibrinogen: 6 nM final; vitronectin: 10 nM final) was pre-mixed in binding buffer (see "Measurement of Aptamer Binding Affinities," above) with varying concentrations of aptamer, control RNA, cyclic RGD peptide, antibody, or unmodified ligand. The mixtures were incubated in the integrin-coated wells for 60 minutes at room temperature. After washing, bound biotinylated ligand was detected by addition of 100 μl/well 1:500 dilution streptavidin-alkaline phosphatase conjugate (Calbiochem) (30 minutes at room temperature) followed by 100 μl/well p-nitrophenyl phosphate, as described above. Absorbance was read at 405 um. The data were fit to an equation that describes mutually exclusive binding of two ligands to a single target species (Gill et al. (1991) J. Mol. Biol. 220:307–24). The concentration of competitor that inhibited 50% of the maximum signal above background (IC$_{50}$) was determined from the fitted curve.

Figure 4B:
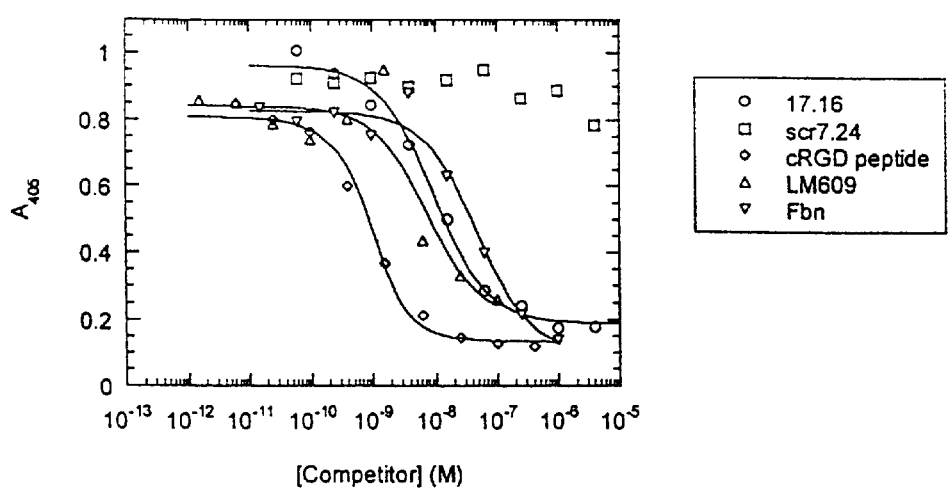
Figure 4C:
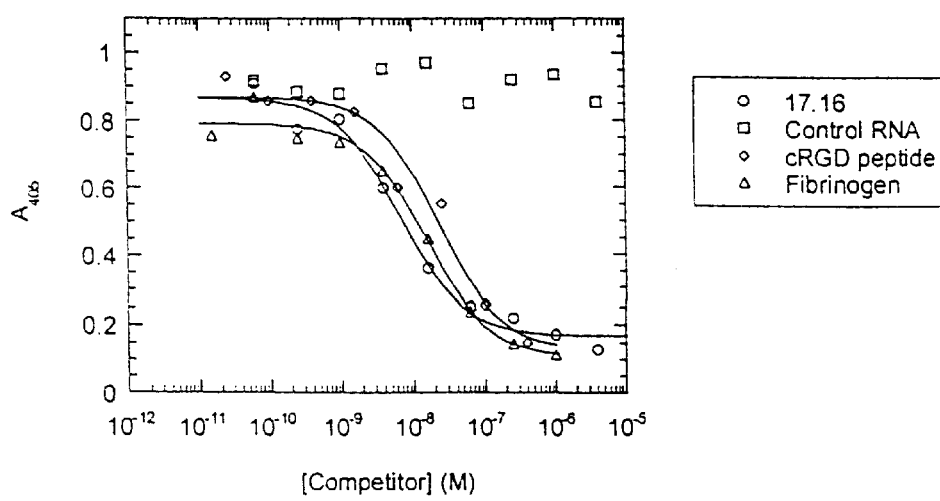

Known ligand binding inhibitors, including an RGD peptide and the $\alpha_v\beta_3$-specific antibody LM609, were included as positive controls for the assay. FIG. 4a shows inhibition of biotinylated vitronectin binding to immobilized $\alpha_v\beta_3$. Aptamer 17.16 inhibited the binding interaction with an IC$_{50}$ of 4.7 nM while the control RNA showed no inhibition. By comparison, the IC$_{50}$ of RGD peptide inhibition was 1.4 nM and that of LM609 was 2.7 nM. Unmodified vitronectin inhibited the binding of the biotinylated material with an IC$_{50}$ of 59 nM. Similar data were obtained for aptamer inhibition of fibrinogen binding to $\alpha_v\beta_3$ (FIG. 4b) and for fibrinogen binding to $\alpha_{IIb}\beta_3$ (FIG. 4c). IC$_{50}$ values for the data in FIG. 4b were: 17.16, 9.5 nM; control RNA, not measurable; RGD peptide, 1.0 nM; LM609, 6.3 nM; unmodified fibrinogen, 43 nM. IC$_{50}$ values for FIG. 4c were: 17.16, 6.5 nM; control RNA, not measurable; RGD peptide, 21 nM; unmodified fibrinogen, 15 nM. Thus, aptamer 17.16 is an effective competitor of $\beta_3$ integrin ligand binding and, on a molar basis, has an inhibitory potency nearly equivalent to that of a bivalent antibody.

Example 5

Nucleic Acid Ligand Binding to Human Platelets

Aptamer 17.16 (SEQ ID NO: 60) was selected for binding to purified human $\alpha_v\beta_3$ adsorbed to the surface of a polystyrene bead. In vitro assays to measure the affinity of the aptamer for purified $\beta_3$ integrins were also done in the context of hydrophobically-adsorbed protein. Thus, an important test of aptamer function was to determine its capacity to bind to native protein on the surface of cells. Human platelets were chosen for this purpose because of their ease of isolation and their high level of expression of integrin $\alpha_{IIb}\beta_3$. Because $\alpha_{IIb}\beta_3$ undergoes a conformational change upon platelet activation, binding of the aptamer to both resting and thrombin-activated platelets was tested. This was done as follow: fluorescein-conjugated RNA was prepared according to (Davis et al. (1998) Nuc. Acids Res. 26:3915–24). Briefly, RNA was transcribed in the presence of a 5-fold molar excess of the initiator nucleotide guanosine-5'-O-(2-thiodiphosphate) (Calciochem), followed by conjugation of the gel-purified RNA to 5-iodoacetamidofluorescein (Pierce, Rockford, Ill.). Platelet-rich plasma was prepared from freshly-drawn citrated human blood by centrifugation at 1000 rpm for 15 minutes in a table top centrifuge. For activated platelets, cells were incubated for 15 minutes at room temperature at 2×10$^7$/ml in calcium- and magnesium-free Dulbecco's PBS with 2.5 U/ml thrombin and 5 mM Gly-Pro-Arg-Pro (GPRP) to inhibit platelet aggregation. Cells were diluted 1:10 into binding buffer (20 mM HEPES, pH 7.5, 111 mM NaCl, 5 mM KCl, 1 mM MgCl$_2$, 1 mM CaCl$_2$, 0.1% BSA, 0.01% NaAzide). Resting cells were diluted similarly, without exposure to thrombin or GPRP. The activation state of resting and thrombin-treated cells was monitored by staining with fluorophore-conjugated antibodies to CD61 ($\beta_3$ integrin subunit), which binds to all platelets, and to CD62 (P-selectin), a marker of platelet activation. Antibodies were obtained from Becton-Dickinson Immunocytometry Systems, San Jose, Calif. Fluorescein-conjugated RNAs were diluted in water to 4 μM and denatured briefly at 93° C., then diluted to 2 μM with 2×-concentrated binding buffer. RNAs were then serially diluted in binding buffer. Each dilution was mixed 1:1 with resting or activated platelets and allowed to incubate in the dark at room temperature for 30 minutes. The incubation mixtures were applied directly to a Becton Dickinson FACSCalibur flow cytometer to determine the mean fluorescence intensity of the sample. Under such equilibrium binding conditions, an estimate of the K$_D$ for aptamer binding to the cell surface integrin could be obtained.

Non-specific RNA binding to platelets was measured using a control RNA of similar length and base composition to aptamer 17.16. Non-specific binding became significant at concentrations above approximately 100 nM. Specific binding of the aptamer was distinguished from non-specific binding by the addition of 5 mM EDTA to the sample: EDTA had no effect on the binding of the control RNA but reduced aptamer binding to the level of the control. Specific binding of the aptamer was thus defined as the difference between the fluorescence intensity of the sample before the addition of EDTA (specific+non-specific) and the fluorescence intensity after the addition of EDTA (non-specific only).

FIG. 5 shows representative data for the EDTA-sensitive component of aptamer binding to both resting and thrombin-activated human platelets. The maximum binding signal is approximately 2-fold higher to activated platelets, consistent with the slightly higher level of $\alpha_{IIb}\beta_3$ on such cells (Wagner et al. (1996) Blood 88:907–14). However, the estimated K$_D$ for aptamer binding to platelets was approximately 10 nM for both cell populations, equivalent to the value determined for binding in vitro to purified $\alpha_{IIb}\beta_3$. Furthermore, aptamer 17.16 binds to both resting and activated platelets with an affinity equivalent to that reported for Reopro (abeiximab, chimeric 7E3 Fab), an approved $\alpha_{IIb}\beta_3$ antagonist (Mousa et al. (1998) J. Pharm. Exp. Ther. 286:1277–84).

Example 6

Nucleic Acid Ligand Biodistribution in Rabbit Venous Clot Model

To explore the application of a $\beta_3$-specific aptamer in clot imaging, aptamer 17.16 was labeled at the 5' end with technitium-99 m ($^{99m}$Tc) and its biodistribution was monitored in a rabbit model of venous thrombosis. In this model, a clot is generated in situ in the isolated jugular vein of a rabbit from human platelet-rich plasma. Blood flow across the clot is re-established and the radiolabeled aptamer (or a non-binding control RNA) are introduced into the bloodstream via the ipsilateral ear vein. The distribution of the radiolabel into various tissues is reported as the per cent of the injected dose per gram of tissue.

The experiment was performed as follows: Aptamer 17.16 and a control RNA of similar length and base composition were transcribed using a 5-fold molar excess of 5'-(O-hexylamino) guanosine monophosphate. Each RNA was conjugated to $Hi_{15}$ at 50 mg/ml aptamer in 30% dimethylformamide with 5 molar equivalents of $Hi_{15}$-NHS buffered in 100 mM NaBorate pH 9.3, for 30 minutes at room temperature. The conjugation reactions were washed over a 30,000 molecular weight cut-off filter (Microcon 30, Amicon, Inc., Beverly, Mass.) to remove excess $Hi_{15}$ cage. The RNAs were then labeled with $^{99m}$Tc in the following manner: to 1 nmol $Hi_{15}$-aptamer was added 200 μl of 100 mM $NaPO_4$ buffer, pH 8.5, 23 mg/ml NaTartrate, and 50 μl [$^{99m}$Tc] pertechnetate (5.0 mCi) eluted from a $^{99}$Mo column (Syncor, Denver) within 12 hours prior to use. The labeling reaction was initiated by the addition of 10 μl 5 mg/ml $SnCl_2$. The reaction mixture was incubated for 15 minutes at 90° C. Unreacted $^{99m}$Tc was removed by spin dialysis through a 30,000 molecular weight cut-off membrane (Centrex, Schleicher & Schuell) with two 300 μl washes. This labeling protocol results in 30–50% of the added $^{99m}$Tc being incorporated with a specific activity of 2–3 mCi/nmol RNA.

For biodistribution studies, rabbits were anesthetized with isofluorane. A two centimeter section of the right jugular vein was isolated in situ and all the branches were ligated. A catheter was inserted into the facial vein. The isolated vein segment was temporarily ligated above and below the catheter. The vein segment was flushed with saline. 1000 USP units of heparin was administered intravenously. 300–400 μl of fresh human platelet-rich plasma (citrate) activated with calcium and thrombin was instilled into the isolated vein segment and allowed to clot. After 30 minutes the ligatures were removed and blood flow over the thrombus was re-established (confirmed by the injection of 200 μl of air into the ipsilateral ear vein). [$^{99m}$Tc]-conjugated aptamer or control RNA was injected into the ipsilateral ear vein. At 1 hr the rabbit was exsanguinated and tissues were weighed and counted in a Wallac 1470 gamma counter. The aptamer and control RNA were tested at 1 nmol/kg (approximately 0.03 mg/kg).

For aptamer 17.16, radiolabel accumulated in the clot to a significant degree by one hour after injection, while similar accumulation was not observed with the control RNA (FIG. 6). Blood clearance of the radiolabel was apparently rapid and mediated primarily by a renal mechanism as judged by moderate accumulation of radioactivity in the kidney for both the aptamer and control RNA. Thus, aptamers specific for $α_{IIb}β_3$ or for other proteins expressed at high levels on the surface of platelets or within the matrix of a clot will serve as useful agents for rapid imaging of thrombi.

TABLE 1

αvβ3 Family 1 aptamer sequences.

Sequence of variable region
5'-gggagacaagaauaaacgcucaa

| Clone name (# of isolates) | [variable region] uucgacaggaggcucacaacaggc-3' | Sequence length | $K_D$ (nM) | SEQ ID NO: |
|---|---|---|---|---|
| 7.3(2) | uucuacgu uguuuaagggcuuauaugagcg-cauuauaccc | 40 | 22 | 5 |
| 7.6; 17.12A | uucaacgc uguuuaagggcu-uauaugagcgcguuacaccc | 40 | ND | 6 |
| 7.12 | uucaacgc uguucaagggcu-uauaugagcgcguuauaccc | 40 | ND | 7 |
| 7.24(5) | uucaacgc uguucaagggcu-uauaugagcgcguuauaccc | 40 | 170 | 8 |
| 7.25 | uucaacga uguuuaagggcu-uauaugagcgcguuauaccc | 40 | ND | 9 |
| 7.34 | uucau gaa guccaagggcu-uauaugagcgcguuauaccc | 39 | ND | 10 |
| 7.36(3) | uucaacgc ugucaaagggcu-uauaugagcgcguuauaccc | 40 | ND | 11 |
| 7.37(2) | uu aacgu uguucaagggu-uuauaugagugcguuauaccc | 39 | ND | 12 |
| 7.38(2) | uucaacgc uguccaagggcu-uauaugagcgcguuauaccc | 40 | 49 | 13 |
| 7.49 | uucaacggauguccaagggcuu uaugagcgcguuauaccc | 40 | ND | 14 |
| 7.53 | uucgacgc uguucaagggcuuauaugagcg-cauuauaucc | 40 | ND | 15 |
| 7.54(2) | uucgacgc uguucaagggcu-uauaugagcgcguuauaccc | 40 | 230 | 16 |
| 7.57(2) | uucgacga uguccaagggcuuauaugagcg-cauuauaccc | 40 | ND | 17 |
| 7.63 | uucaacgc uguucaagggcu-uauaugagcgcguuacaccc | 40 | ND | 18 |
| 7.64 | uuc auga uguucaagggcuuauaugagcg-cauuauaccc | 39 | ND | 19 |
| 7.77(2) | uucaacga uguugagggcuuauaugagcg-cauuauaccc | 40 | 770 | 20 |
| 7.80 | uucaacga uguccaagggcuuauaugagcg-cauuauaccc | 40 | ND | 21 |

TABLE 1-continued

αvβ3 Family 1 aptamer sequences.

Sequence of variable region
5'-gggagacaagaauaaacgcucaa
[variable region]
uucgacaggaggcucacaacaggc-3'

| Clone name (# of isolates) | [variable region] | Sequence length | K_D (nM) | SEQ ID NO: |
|---|---|---|---|---|
| 7.86 | uucaacgc uguucaagggcuuau-gugagcgcguuauaccc | 40 | ND | 22 |
| 7.91 | uucaacgc uguccaagggcuuauaugagcg-cauuauaccc | 40 | ND | 23 |
| 7.115 | uucaacgc uguucaagggcuuauaugagcg-cauuauaccc | 40 | ND | 24 |
| 7.121 | uucaacga uguccaagggcuuauaugagcg-gauua ccc | 38 | ND | 25 |
| 7.124 | uucaacac ugu gaagggcu-uauaugagcgcgucauaccc | 39 | ND | 26 |
| 7.127 | uucaacgu ugu ucaagggcu-uauaugagcgcguuauaccc | 40 | ND | 27 |
| 15.2 | uucaacgu ugucaaagggcuuauaugagcg-gauua ccc | 38 | 6 | 28 |
| 15.3(3);17.17 | uucaacgu uguccaagggcuuauaugagcg-gauua ccc | 38 | 8 | 29 |
| 15.7 | uucuacga ugucaaagggcuuauaugagcg-gauua ccc | 38 | 5 | 30 |
| 15.8 | uucgacgc uguugaagggcuuauacgagcg-gauua ccc | 38 | 5 | 31 |
| 15.10 | uucaacgc uguucaagggcuuauaugagcg-gauua ccc | 38 | 20 | 32 |
| 15.14 | uucaacau uguccaagggcuuauaugagcg-gauua ccc | 38 | 6 | 33 |
| 15.17 | uucaacgu ugucaaagggcuuauacgggcg-gauua ccc | 38 | 4 | 34 |
| 15.18(2) | uucaacgc ugug aagggcuuauaugagcg-gauua ccc | 37 | 2 | 35 |
| 15.20 | uucaacgc uguccaagggcuuauaugagcg-cauuauaccc | 40 | 20 | 36 |
| 15.27 | uucgacua uguccaagggcuuauaugagcg-gauua ccc | 38 | ND | 37 |
| 15.28 | uucgacga ugucuaagggcuuauaugagcg-gauua ccc | 38 | ND | 38 |
| 15.40;17.12B | uucaacgc uguugaagggcuuauacgagcg-gauua ccc | 38 | ND | 39 |
| 15.41 | uucaacgu uguccaagggcuuauacgagcg-gauua ccc | 38 | ND | 40 |
| 15.42;17.14(2) | uuacaacgu uguccaagggcuuauacgagcg-gauua ccc | 38 | ND | 41 |
| 15.46;17.20 | uucgacgc ugug aagggcuuauaugagcg-gauua ccc | 37 | 40 | 42 |
| 15.47 | uucaacgu ugucaaagggcuuauacgagcg-gauua ccc | 38 | ND | 43 |
| 15.48 | uucaacgc uguugaagggcuuauaugagcg-gauua ccc | 38 | ND | 44 |
| 15.49 | uucuacgu ugucuaagggcuuauaugagcg-gauua ccc | 38 | ND | 45 |
| 15.50;17.3 | uucgacgc ugug aagggcuuauacgagcg-gauua ccc | 37 | 30 | 46 |
| 15.52 | uucaacgc uguucaagggcuuauacgagcg-gauua ccc | 38 | ND | 47 |
| 15.53 | uucaacgc uguccuagggcuuauaugagcg-caggauaccc | 40 | 70 | 48 |
| 15.55 | uucuacgc uguuuaagggcuuauaugagc-gaauua ccc | 38 | ND | 49 |
| 15.57 | uucuacgu uguccaagggcuuauaugagcg-gauua ccc | 38 | ND | 50 |
| 15.58 | uucgacgu uguugaagggcuuauaugagcg-gauua ccc | 38 | ND | 51 |
| 17.1 | uucaacgc ugucaaagggcuuauauaagcg-gauua ccc | 38 | 380 | 52 |
| 17.2(2) | uucuacgc ugug aagggcuuauaugagcg-gauua ccc | 37 | 2 | 53 |
| 17.5 | uucgacgc ugug aagggcuuauaugagcg-gau acaccc | 38 | 5 | 54 |
| 17.7(2) | uucuacgc ugug aagggcuuauacgagcg-gauua ccc | 37 | 6 | 55 |
| 17.8 | uucaacgu ugucuaagggcuuauaugagcg-gauua ccc | 38 | 18 | 56 |
| 17.10 | uucuacgu uguugaagggcuuauaugagcg-gauua ccc | 38 | ND | 57 |
| 17.11 | uucaacgc ugug aagggcuuauaugagc-gaauua ccc | 37 | 4 | 58 |
| 17.13 | uucaacgc uguccaagggcuuauaugggcg-gauua ccc | 38 | 10 | 59 |

TABLE 1-continued

αvβ3 Family 1 aptamer sequences.

| Clone name (# of isolates) | Sequence of variable region 5'-gggagacaagaauaaacgcucaa [variable region] uucgacaggaggcucacaacaggc-3' | Sequence length | K_D (nM) | SEQ ID NO: |
|---|---|---|---|---|
| 17.16 | uucaacgc ugug aagggcuuauacgagcg-gauua ccc | 37 | 8 | 60 |

TABLE 2

αvβ3 Family 2 aptamer sequences

| Clone name (# of isolates) | Sequence of variable region 5'-gggagacaagaauaaacgcucaa [variable region] uucgacaggaggcucacaacaggc-3' | Sequence length | K_D (nM) | SEQ ID NO: |
|---|---|---|---|---|
| 7.4 | GUACCGGAUCGCCCUGCCACGUAUUUGAGACAUUGAAA | 39 | ND | 61 |
| 7.5(3) | GGUAGUAAAUGGACUCCUGCCAUCCAAUACUAUCUCUGAG | 40 | >1000 | 62 |
| 7.13 | UGUAGUCGCAUGUCGAGCAGCAAUUCCUGCCAUUGUAGG | 39 | >1000 | 63 |
| 7.14(2) | UGAAGAACUAGACCUGCCCAAGUCCUUCAUCGUGCUUGCU | 40 | ND | 64 |
| 7.27(2) | CGAUUAUACUAUCCCUGCCAGUAGUAAUCAGUGCUAUA | 38 | ND | 65 |
| 7.29 | CGGUGAAGACCUCUAUUAACAACAUGACCUGCCUGCGUUG | 40 | ND | 66 |
| 7.32 | CGCAAAUAUGUUCCUGCCAAAUACGGGCGUUGACGCUAGA | 40 | ND | 67 |
| 7.43 | GGACCCUGCCGAGCACAUUUAUUCUGGUAACUGAGCCCCC | 40 | ND | 68 |
| 7.51 | CGCUGAGAGAAAGCCCUGCCCUUUCAGCUCGAGAGUUAUA | 40 | ND | 69 |
| 7.58 | UGAGAUGCAGUUCCUGCCUGCUGCAUUUCUUAGAGUGUGU | 40 | ND | 70 |
| 7.83 | GAUUAACGGUUAUCCUGCCAACCGAUUAUAAGAGCAUGGA | 40 | ND | 71 |
| 7.89 | UGAGAGACUACAAUAGAACUUAUGUAACCUGCCACAUAGG | 40 | ND | 72 |
| 7.97 | UAGGAAGUGUAACCUGCCUCACGGUCCUAUCGAGUAGUUU | 40 | ND | 73 |
| 7.100 | UGAAAACGCAACCUGCCGGCGUCGUCCUUUGGGUAAUUUA | 40 | ND | 74 |
| 7.104 | AUAGGGGUUACCUGCCGACCCCAGAAAUAAGCGUGAUU | 39 | ND | 75 |
| 7.105 | UCCUGCCAUAGCGUCUUCAUGUCUGACGUUUGAGUUUCCG | 40 | ND | 76 |
| 7.107 | UCCUAGGUUGGUCCUGCCACAGCUCAAAGGUUUAGCUUCA | 40 | ND | 77 |
| 7.109 | ACAUGCAGACAACCCUGCCUUCUGCGUGGUUUAGGAGUA | 39 | ND | 78 |
| 7.120 | AACCUCAGGCGACCUGCCGCUGUCUGAAGUUCGAGCAUAA | 40 | ND | 79 |
| 7.122 | ACUCAAGACCCUGCCACUAUGUGUUUACUGAGUAGGAGCGU | 40 | ND | 80 |
| 7.125 | AUUCGAAAUACGGGUUAAAUCCCUGCCUUUAACACGACA | 39 | ND | 81 |
| 15.19 | UGUAGCCGCAUGUCGAGCAGCAAUUCCUGCCAUUGUAGG | 39 | 770 | 82 |
| 15.21 | CGGUGAAGACCUCUAUUAACAACAUGACCUGCCUGCGUUG | 40 | 200 | 83 |
| 15.34 | UCCCACCCUGCCUUGUCUGUUUGAUAGAGACACUGUCCUU | 40 | 190 | 84 |

TABLE 3

αvβ3 orphan aptamer sequences

| Clone name (# of isolates) | Sequence of variable region 5'-gggagacaagaauaaacgcucaa [variable region] uucgacaggaggcucacaacaggc-3' | Sequence length | K_D (nM) | SEQ ID NO: |
|---|---|---|---|---|
| 7.1 | gguuugaaagauugccuguagcuccaaaucuuggugagcu | 40 | ND | 85 |
| 7.2 | ucccgccgauagcuuccacgaagaguuaucguaaaacaa | 40 | ND | 86 |
| 7.11 | ugagcuccugauuccaaaccuauuccguuucgggu | 36 | ND | 87 |
| 7.30 | acuggacaagucaaucucuccggcuugagacuuggUUUAC | 40 | ND | 88 |
| 7.33(2) | cgagcucuugcuuccaaaccuauuccagacguuu cuggg | 40 | ND | 89 |
| 7.41(2) | gcgagccuauugucuaagaugcaccaggccuguuaagcau | 40 | >1000 | 90 |
| 7.42 | gccuguacggcgauuaugucuuuaccuuaacuguucc | 37 | ND | 91 |
| 7.46 | uaccaauggcacgaauaacugacuaccccccaaaauggaa | 40 | ND | 92 |
| 7.47 | gcggggcuuugcucaaguguuugcaaacguaaaauuccac | 40 | ND | 93 |
| 7.61 | ccuaccgacguccgccgcuggguuaaccuguaaaagucacu | 40 | ND | 94 |
| 7.66(2) | gugaaccgauaagcgaaaguaguaccccugccuugacuacu | 40 | >1000 | 95 |
| 7.67 | ggagcuccuaguuccaaaccuauuccagaaguuuucgggu | 41 | ND | 96 |
| 7.75 | uaguacgcagucauagcggggcagggacuuucuccgugca | 40 | ND | 97 |
| 7.76 | uuauacugguaugccgccgaccagaauuaaccaaugcgu | 40 | ND | 98 |
| 7.82 | ugagcuccugguuccaaaccuauuccagacguuucagggu | 40 | ND | 99 |
| 7.85 | ucuggccugugacuguagucguuucuucgaguugugacgc | 40 | ND | 100 |
| 7.92 | cucaacgauguccaagggcuuauaugagcgcguuacccc | 39 | ND | 101 |
| 7.93 | gcgagccuauugucuaagaugcgccaagccuguaaagcau | 40 | ND | 102 |
| 7.94 | gacuagccggccugagauccuuguucgccacacaugcugg | 40 | ND | 103 |

TABLE 3-continued

αvβ3 orphan aptamer sequences

| Clone name (# of isolates) | Sequence of variable region 5'-gggagacaagaauaaacgcucaa [variable region] uucgacaggaggcucacaacaggc-3' | Sequence length | $K_D$ (nM) | SEQ ID NO: |
|---|---|---|---|---|
| 7.96 | cuuccccgcaaacacauguuuaguacugggagacuuggg | 40 | ND | 104 |
| 7.101 | ugagcuccugauuccgaaccuauuccagacguuucuggu | 40 | ND | 105 |
| 7.102 | cugauccucuugucauuguacaucucgcag | 30 | ND | 106 |
| 7.106 | uacuaagccuaacaaaagagcggauauuggcgcggcacg | 39 | ND | 107 |
| 7.108 | agucuuaguaguaccgccugcuucuaaccuugggcgcuuu | 40 | ND | 108 |
| 7.112 | ugauuucaugacuuaugccgccggcaugacuucaaugacg | 40 | ND | 109 |
| 7.114 | ucaaaggacggaagugccugugcccgacuaaagaguugag | 40 | ND | 110 |
| 7.118 | cuaucgaucguuuuucauuuccccugaccaucgccug | 39 | ND | 111 |
| 7.123 | uugucccgcgcagaaacgugacaaauuuaacacgcaccgu | 40 | ND | 112 |
| 7.128 | uucaacguuguucaagggcuuauaugagcgcguuauaccc | 40 | ND | 113 |
| 15.4(4) | ugauuucaugacuuaugccgccggcaugacuucaaugacg | 40 | 2000 | 114 |
| 15.5 | gcauucaaaauuugcgagaacgaauagaaguccgagagcc | 40 | 4000 | 115 |
| 15.13(2) | gcgggauuuuccugaucaucccacugauucggggccuuac | 40 | 790 | 116 |
| 15.39 | ucaaucucggacuagacuaacgaccuugguugacgcuca | 39 | 410 | 117 |
| 15.43 | cgccguuaucacgacgugcguucugggcgguacucgcgca | 40 | 45 | 118 |

What is claimed is:

1. A nucleic acid ligand to an integrin identified according to the method comprising:
   a) preparing a candidate mixture of nucleic acids;
   b) contacting the candidate mixture of nucleic acids with said integrin, wherein nucleic acids having an increased affinity to said integrin relative to the candidate mixture may be partitioned from the remainder of the candidate mixture;
   c) partitioning the increased affinity nucleic acids from the remainder of the candidate mixture;
   d) amplifying the increased affinity nucleic acids to yield a mixture of nucleic acids enriched for nucleic acids with relatively higher affinity and specificity for binding to said integrin, whereby a nucleic acid ligand of said integrin may be identified.

2. The nucleic acid ligand of claim 1 wherein said integrin is a $\beta_3$ integrin.

3. The nucleic acid ligand of claim 2 wherein said $\beta_3$ integrin is selected from the group consisting of $\alpha_{IIb}\beta_3$ integrin and $\alpha_v\beta_3$ integrin.

4. A purified and isolated non-naturally occurring nucleic acid ligand to an integrin.

5. A purified and non-naturally occurring RNA ligand to an integrin wherein said ligand is selected from the group consisting of SEQ ID NO:5–118.

6. The nucleic acid ligand of claim 1 wherein said integrin is attached through either covalent or non-covalent bonds to a solid support, and wherein steps b)–c) take place on the surface of said solid support.

7. The nucleic acid ligand of claim 6 wherein said solid support is a bead.

8. The nucleic acid ligand of claim 1 wherein said candidate mixture of nucleic acids is comprised of single stranded nucleic acids.

9. The nucleic acid ligand of claim 8 wherein said single stranded nucleic acids are ribonucleic acids.

10. The nucleic acid ligand of claim 8 wherein said single stranded nucleic acids are deoxyribonucleic acids.

11. The nucleic acid ligand of claim 9 wherein said candidate mixture of nucleic acids comprises 2'-F(2'-fluoro) modified ribonucleic acids.

12. The purified and isolated non-naturally occurring nucleic acid ligand of claim 4 wherein said nucleic acid ligand is single stranded.

13. The purified and isolated non-naturally occurring nucleic acid ligand of claim 12 wherein said nucleic acid ligand is RNA.

14. The purified and isolated non-naturally occurring RNA ligand of claim 13 wherein said ligand is comprised of 2'-fluoro (2'-F) modified nucleotides.

15. A method for the isolation of nucleic acid ligands to an integrin, comprising:
   a) preparing a candidate mixture of nucleic acids;
   b) contacting the candidate mixture of nucleic acids with said integrin, wherein nucleic acids having an increased affinity to said integrin relative to the candidate mixture may be partitioned from the remainder of the candidate mixture;
   c) partitioning the increased affinity nucleic acids from the remainder of the candidate mixture;
   d) amplifying the increased affinity nucleic acids to yield a mixture of nucleic acids enriched for nucleic acids with relatively higher affinity and specificity for binding to said integrin, whereby a nucleic acid ligand of said integrin may be isolated; and
   e) isolating nucleic acid ligands to an integrin.

16. The method of claim 15 wherein said candidate mixture comprises single-stranded nucleic acids.

17. The method of claim 16 wherein said single-stranded nucleic acids comprise ribonucleic acids.

18. The method of claim 15 wherein said integrin is a $\beta_3$ integrin.

19. The method of claim 18 wherein said $\beta_3$ integrin is $\alpha_{IIb}\beta_3$ integrin.

* * * * *

SEQUENCE LISTING

<160> NUMBER OF SEQ ID NOS: 118

<210> SEQ ID NO 1
<211> LENGTH: 104
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(104)
<223> OTHER INFORMATION: N at positions 41-80 is any base

<400> SEQUENCE: 1
ttatacgact cactataggg agacaagaat aaacgctcaa nnnnnnnnnn nnnnnnnnnn      60
nnnnnnnnnn nnnnnnnnnn ttcgacagga ggctcacaac aggc                     104

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 2
gcctgttgtg agcctcctgt cgaa                                            24

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
taatacgact cactataggg agacaagaat aaacgctcaa                           40

<210> SEQ ID NO 4
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 4
gggagacaag aauaaucgcu caacguugaa ugcugcauua uggaguauug accgcuacau    60
cccuucgaca ggaggcucac aacaggc                                       87

<210> SEQ ID NO 5
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 5
gggagacaag aauaaacgcu caauucuacg uuguuuaagg gcuuauauga gcgcauuaua    60
cccuucgaca ggaggcucaa caggc                                         85

<210> SEQ ID NO 6
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 6
gggagacaag aauaaacgcu caauucaacg cuguuuaagg gcuuauauga gcgcguuaua    60
cccuucgaca ggaggcucaa caggc                                         85

<210> SEQ ID NO 7
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 7
gggagacaag aauaaacgcu caauucaacg cuguuuaagg gcuuauauga gcgcguuaca    60
cccuucgaca ggaggcucac aacaggc                                       87

<210> SEQ ID NO 8
<211> LENGTH: 85
<212> TYPE: RNA

```
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 8
gggagacaag aauaaacgcu caauucaacg cuguucaagg gcuuauauga gcgcguuaua      60
cccuucgaca ggaggcucaa caggc                                           85

<210> SEQ ID NO 9
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 9
gggagacaag aauaaacgcu caauucaacg auguuuaagg gcuuauauga gcgcguuaua      60
cccuucgaca ggaggcucac aacaggc                                         87

<210> SEQ ID NO 10
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 10
gggagacaag aauaaacgcu caauucauga aguccaaggg cuuauaugag cgcguuauac      60
ccuugacagg aggcucacaa caggc                                           85

<210> SEQ ID NO 11
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 11
gggagacaag aauaaacgcu caauucaacg cgucaaagg gcuuauauga gcgcguuaua       60
cccuugacag gaggcucaca acaggc                                          86

<210> SEQ ID NO 12
<211> LENGTH: 86
<212> TYPE: RNA
<213> ORGANISM: Artificial Sequence
<220> FEATURE:
<223> OTHER INFORMATION: Description of Artificial Sequence: Synthetic
```

```
        Sequence
<220> FEATURE:
<221> NAME/KEY: modified_base
<222> LOCATION: (1)..(86)
<223> OTHER INFORMATION: All pyrimidines are 2' F.

<400> SEQUENCE: 12
gggagacaag aauaaacgcu caauuaacgu uguucaaggg uuuauaugag ugcguuauac    60
ccuucgacag gaggcucaca acaggc                                        86

<210> SEQ ID NO 13
<211> LENGTH: 87
<212> TYPE: RNA
<213> ORGANISM: Artificial Sequence
<220> FEATURE:
<223> OTHER INFORMATION: Description of Artificial Sequence: Synthetic
        Sequence
<220> FEATURE:
<221> NAME/KEY: modified_base
<222> LOCATION: (1)..(87)
<223> OTHER INFORMATION: All pyrimidines are 2' F.

<400> SEQUENCE: 13
gggagacaag aauaaacgcu caauucaacg cuguccaagg gcuuauauga gcgcguuaua    60
cccuucgaca ggaggcucac aacaggc                                       87

<210> SEQ ID NO 14
<211> LENGTH: 87
<212> TYPE: RNA
<213> ORGANISM: Artificial Sequence
<220> FEATURE:
<223> OTHER INFORMATION: Description of Artificial Sequence: Synthetic
        Sequence
<220> FEATURE:
<221> NAME/KEY: modified_base
<222> LOCATION: (1)..(87)
<223> OTHER INFORMATION: All pyrimidines are 2' F.

<400> SEQUENCE: 14
gggagacaag aauaaacgcu caauucaacg gauguccaag ggcuuuauga gcgcguuaua    60
cccuucgaca ggaggcucac aacaggc                                       87

<210> SEQ ID NO 15
<211> LENGTH: 87
<212> TYPE: RNA
<213> ORGANISM: Artificial Sequence
<220> FEATURE:
<223> OTHER INFORMATION: Description of Artificial Sequence: Synthetic
        Sequence
<220> FEATURE:
<221> NAME/KEY: modified_base
<222> LOCATION: (1)..(87)
<223> OTHER INFORMATION: All pyrimidines are 2' F.

<400> SEQUENCE: 15
gggagacaag aauaaacgcu caauucgacg cuguucaagg gcuuauauga gcgcauuaua    60
uccuucgaca ggaggcucac aacaggc                                       87

<210> SEQ ID NO 16
<211> LENGTH: 87
<212> TYPE: RNA
<213> ORGANISM: Artificial Sequence
<220> FEATURE:
<223> OTHER INFORMATION: Description of Artificial Sequence: Synthetic
        Sequence
<220> FEATURE:
<221> NAME/KEY: modified_base
```

```
<222> LOCATION: (1)..(87)
<223> OTHER INFORMATION: All pyrimidines are 2' F.

<400> SEQUENCE: 16
gggagacaag aauaaacgcu caauucgacg cuguucaagg gcuuauauga gcgcguuaua      60
cccuucgaca ggaggcucac aacaggc                                         87

<210> SEQ ID NO 17
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 17
gggagacaag aauaaacgcu caauucgacg auguccaagg gcuuauauga gcgcauuaua      60
cccuucgaca ggaggcucac aacaggc                                         87

<210> SEQ ID NO 18
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 18
gggagacaag aauaaacgcu caauucaacg cuguucaagg gcuuauauga gcgcguuaca      60
cccuucgaca ggaggcucac aacaggc                                         87

<210> SEQ ID NO 19
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 19
gggagacaag aauaaacgcu caauucauga uguucaaggg cuuauaugag cgcauuauac      60
ccuucgacag gaggcucaca acaggc                                          86

<210> SEQ ID NO 20
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.
```

```
<400> SEQUENCE: 20
gggagacaag aauaaacgcu caauucaacg auguugaggg gcuuauauga gcgcauuaua        60
cccuucgaca ggaggcucac aacaggc                                           87

<210> SEQ ID NO 21
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 21
gggagacaag aauaaacgcu caauucaacg auguccaagg gcuuauauga gcgcauuaua        60
cccuucgaca ggaggcucac aacaggc                                           87

<210> SEQ ID NO 22
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 22
gggagacaag aauaaacgcu caauucaacg cuguucaagg gcuuauguga gcgcguuaua        60
cccuucgaca ggaggcucac aacaggc                                           87

<210> SEQ ID NO 23
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 23
gggagacaag aauaaacgcu caauucaacg uuguccaagg gcuuauauga gcgcauuaua        60
cccuucgaca ggaggcucac aacaggc                                           87

<210> SEQ ID NO 24
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 24
gggagacaag aauaaacgcu caauucaacg cuguucaagg gcuuauauga gcgcauuaua        60
```

```
cccuucgaca ggaggcucac aacaggc                                           87
```

<210> SEQ ID NO 25
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 25

```
gggagacaag aauaaacgcu caauucaacg auguccaagg gcuuauauga gcggauuacc       60
cuucgacagg aggcucacaa caggc                                            85
```

<210> SEQ ID NO 26
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 26

```
gggagacaag aauaaacgcu caauucaaca cugugaaggg cuuauaugag cgcgucauac       60
ccuucgacag gaggcucaca acaggc                                           86
```

<210> SEQ ID NO 27
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 27

```
gggagacaag aauaaacgcu caauucaacg uuguucaagg gcuuauauga gcgcguuaua       60
cccuucgaca ggaggcucac aacaggc                                          87
```

<210> SEQ ID NO 28
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 28

```
gggagacaag aauaaacgcu caauucaacg uugucaagg gcuuauauga gcggauuacc        60
cuucgacagg aggcucacaa caggc                                            85
```

<210> SEQ ID NO 29
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 29
gggagacaag aauaaacgcu caauucaacg uuguccaagg gcuuauauga gcggauuacc    60
cuucgacagg aggcucacaa caggc                                         85

<210> SEQ ID NO 30
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 30
gggagacaag aauaaacgcu caauucuacg augucaaagg gcuuauauga gcggauuacc    60
cuucgacagg aggcucacaa caggc                                         85

<210> SEQ ID NO 31
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 31
gggagacaag aauaaacgcu caauucgacg cuguugaagg gcuuauacga gcggauuacc    60
cuucgacagg aggcucacaa caggc                                         85

<210> SEQ ID NO 32
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 32
gggagacaag aauaaacgcu caauucaacg cuguucaagg gcuuauauga gcggauuacc    60
cuucgacagg aggcucacaa caggc                                         85

<210> SEQ ID NO 33
<211> LENGTH: 85

```
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 33
gggagacaag aauaaacgcu caauucaaca uuguccaagg gcuuauauga gcggauuacc      60
cuucgacagg aggcucacaa caggc                                            85

<210> SEQ ID NO 34
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 34
gggagacaag aauaaacgcu caauucaacg uugucaaagg gcuuauacgg gcggauuacc      60
cuucgacagg aggcucacaa caggc                                            85

<210> SEQ ID NO 35
<211> LENGTH: 84
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(84)
<223> OTHER INFORMATION: All pyrimidines are 2' F.

<400> SEQUENCE: 35
gggagacaag aauaaacgcu caauucaacg cugugaaggg cuuauaugag cggauuaccc      60
uucgacagga ggcucacaac aggc                                             84

<210> SEQ ID NO 36
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 36
gggagacaag aauaaacgcu caauucaacg cuguccaagg gcuuauauga gcgcauuaua      60
cccuucgaca ggaggcucac aacaggc                                          87

<210> SEQ ID NO 37
<211> LENGTH: 85
<212> TYPE: RNA
<213> ORGANISM: Artificial Sequence
<220> FEATURE:
```

```
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 37
gggagacaag aauaaacgcu caauucgacu auguccaagg gcuuauauga gcggauuacc     60
cuucgacagg aggcucacaa caggc                                          85

<210> SEQ ID NO 38
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 38
gggagacaag aauaaacgcu caauucgacg augucuaagg gcuuauauga gcggauuacc     60
cuucgacagg aggcucacaa caggc                                          85

<210> SEQ ID NO 39
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 39
gggagacaag aauaaacgcu caauucaacg cuguugaagg gcuuauacga gcggauuacc     60
cuucgacagg aggcucacaa caggc                                          85

<210> SEQ ID NO 40
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 40
gggagacaag aauaaacgcu caauucaacg uuguccaagg gcuuauacga gcggauuacc     60
cuucgacagg aggcucacaa caggc                                          85

<210> SEQ ID NO 41
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
```

<221> NAME/KEY: modified_base
<222> LOCATION: (1)..(85)
<223> OTHER INFORMATION: All pyrimidines are 2' F.

<400> SEQUENCE: 41
gggagacaag aauaaacgcu caauucaacg cuguccaagg gcuuauacga gcggauuacc    60
cuucgacagg aggcucacaa caggc                                          85

<210> SEQ ID NO 42
<211> LENGTH: 84
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(84)
<223> OTHER INFORMATION: All pyrimidines are 2' F.

<400> SEQUENCE: 42
gggagacaag aauaaacgcu caauucgacg cugugaaggg cuuauaugag cggauuaccc    60
uucgacagga ggcucacaac aggc                                           84

<210> SEQ ID NO 43
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 43
gggagacaag aauaaacgcu caauucaacg uugucaaagg gcuuauacga gcggauuacc    60
cuucgacagg aggcucacaa caggc                                          85

<210> SEQ ID NO 44
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 44
gggagacaag aauaaacgcu caauucaacg cuguugaagg gcuuauauga gcggauuacc    60
cuucgacagg aggcucacaa caggc                                          85

<210> SEQ ID NO 45
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 45
gggagacaag aauaaacgcu caauucuacg uugucuaagg gcuuauauga gcggauuacc    60
cuucgacagg aggcucacaa caggc    85

<210> SEQ ID NO 46
<211> LENGTH: 84
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(84)
<223> OTHER INFORMATION: All pyrimidines are 2' F.

<400> SEQUENCE: 46
gggagacaag aauaaacgcu caauucgacg cugugaaggg cuuauacgag cggauuaccc    60
uucgacagga ggcucacaac aggc    84

<210> SEQ ID NO 47
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 47
gggagacaag aauaaacgcu caauucaacg cuguucaagg gcuuauacga gcggauuacc    60
cuucgacagg aggcucacaa caggc    85

<210> SEQ ID NO 48
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 48
gggagacaag aauaaacgcu caauucaacg cguccuagg gcuuauauga gcgcaggaua    60
cccuucgaca ggaggcucac aacaggc    87

<210> SEQ ID NO 49
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 49
gggagacaag aauaaacgcu caauucuacg cuguuuaagg gcuuauauga gcgaauuacc    60
cuucgacagg aggcucacaa caggc    85

<210> SEQ ID NO 50
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 50
gggagacaag aauaaacgcu caauucuacg uuguccaagg gcuuauauga gcggauuacc    60
cuucgacagg aggcucacaa caggc    85

<210> SEQ ID NO 51
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 51
gggagacaag aauaaacgcu caauucgacg uuguugaagg gcuuauauga gcggauuacc    60
cuucgacagg aggcucacaa caggc    85

<210> SEQ ID NO 52
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 52
gggagacaag aauaaacgcu caauucaacg cugucaaagg gcuuauauaa gcggauuacc    60
cuucgacagg aggcucacaa caggc    85

<210> SEQ ID NO 53
<211> LENGTH: 84
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(84)
<223> OTHER INFORMATION: All pyrimidines are 2' F.

<400> SEQUENCE: 53
gggagacaag aauaaacgcu caauucuacg cugugaaggg cuuauaugag cggauuaccc    60
uucgacagga ggcucacaac aggc    84

<210> SEQ ID NO 54
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 54
gggagacaag aauaaacgcu caauucgacg cugugaaggg cuuauaugag cggauacacc    60
cuucgacagg aggcucacaa caggc                                         85

<210> SEQ ID NO 55
<211> LENGTH: 84
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(84)
<223> OTHER INFORMATION: All pyrimidines are 2' F.

<400> SEQUENCE: 55
gggagacaag aauaaacgcu caauucuacg cugugaaggg cuuauacgag cggauuaccc    60
uucgacagga ggcucacaac aggc                                          84

<210> SEQ ID NO 56
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 56
gggagacaag aauaaacgcu caauucaacg uugucuaagg gcuuauauga gcggauuacc    60
cuucgacagg aggcucacaa caggc                                         85

<210> SEQ ID NO 57
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 57
gggagacaag aauaaacgcu caauucuacg uuguugaagg gcuuauauga gcggauuacc    60
cuucgacagg aggcucacaa caggc                                         85

<210> SEQ ID NO 58

```
<211> LENGTH: 84
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(84)
<223> OTHER INFORMATION: All pyrimidines are 2' F.

<400> SEQUENCE: 58
gggagacaag aauaaacgcu caauucuacg cugugaaggg cuuauaugag cgaauuaccc    60
uucgacagga ggcucacaac aggc                                          84

<210> SEQ ID NO 59
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 59
gggagacaag aauaaacgcu caauucaacg cuguccaagg gcuuauaugg gcggauuacc    60
cuucgacagg aggcucacaa caggc                                         85

<210> SEQ ID NO 60
<211> LENGTH: 84
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(84)
<223> OTHER INFORMATION: All pyrimidines are 2' F.

<400> SEQUENCE: 60
gggagacaag aauaaacgcu caauucaacg cugugaaggg cuuauacgag cggauuaccc    60
uucgacagga ggcucacaac aggc                                          84

<210> SEQ ID NO 61
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 61
gggagacaag aauaaacgcu caaguaccgg aucgcccugc cacgguauuu gagacauuga    60
aauucgacag gaggcucaca acaggc                                        86

<210> SEQ ID NO 62
<211> LENGTH: 87
<212> TYPE: RNA
<213> ORGANISM: Artificial Sequence
```

```
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 62
gggagacaag aauaaacgcu caagguagua aauggacucc ugccauccaa uacuaucucu      60
gaguucgaca ggaggcucac aacaggc                                         87

<210> SEQ ID NO 63
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 63
gggagacaag aauaaacgcu caauguaguc gcaugucgag cagcaauucc ugccauugua      60
gguucgacag gaggcucaca acaggc                                          86

<210> SEQ ID NO 64
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 64
gggagacaag aauaaacgcu caaugaagaa cuagaccugc ccaagaccuu caucgugcuu      60
gcuuucgaca ggaggcucac aacaggc                                         87

<210> SEQ ID NO 65
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(85)
<223> OTHER INFORMATION: All pyrimidines are 2' F.

<400> SEQUENCE: 65
gggagacaag aauaaacgcu caacgauuau acuaucccug ccaguaguaa ucagugcuau      60
auucgacagg aggcucacaa caggc                                           85

<210> SEQ ID NO 66
<211> LENGTH: 88
<212> TYPE: RNA
<213> ORGANISM: Artificial Sequence
<220> FEATURE:
<223> OTHER INFORMATION: Description of Artificial Sequence: Synthetic
      Sequence
```

<220> FEATURE:
<221> NAME/KEY: modified_base
<222> LOCATION: (1)..(88)
<223> OTHER INFORMATION: All pyrimidines are 2' F.

<400> SEQUENCE: 66
gggagacaag aauaaacgcu caacggugaa gaccucuauu aacaacauga ccugccugcg        60
uugauucgac aggaggcuca caacaggc        88

<210> SEQ ID NO 67
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 67
gggagacaag aauaaacgcu caacgcaaau auguccugc caaauacggg cguugacgcu        60
agauucgaca ggaggcucac aacaggc        87

<210> SEQ ID NO 68
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 68
gggagacaag aauaaacgcu caaggacccu gccgagcaca uuuauucugg uaacugagcc        60
cccuucgaca ggaggcucac aacaggc        87

<210> SEQ ID NO 69
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 69
gggagacaag aauaaacgcu caacgcugag agaaagcccu gcccuuucag cucgagaguu        60
auauucgaca ggaggcucac aacaggc        87

<210> SEQ ID NO 70
<211> LENGTH: 88
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(88)

<223> OTHER INFORMATION: All pyrimidines are 2' F.

<400> SEQUENCE: 70
gggagacaag aauaaacgcu caaugagaug caguuccugc cugcugcauu ucuuagagug    60
uguauucgac aggaggcuca caacaggc                                      88

<210> SEQ ID NO 71
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 71
gggagacaag aauaaacgcu caagauuaac gguuauccug ccaaccgauu auaagagcau    60
ggauucgaca ggaggcucac aacaggc                                       87

<210> SEQ ID NO 72
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 72
gggagacaag aauaaacgcu caaugagaga cuacaauaga acuuauguaa ccugccacau    60
agguucgaca ggaggcucac aacaggc                                       87

<210> SEQ ID NO 73
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 73
gggagacaag aauaaacgcu caauaggaag uguaaccugc cucacgqucc uaucgaguag    60 uuuuucgaca ggaggcucac aacaggc                                       87

<210> SEQ ID NO 74
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 74
gggagacaag aauaaacgcu caaugaaaac gcaaccugcc ggcgucgucc uuuggguaau    60
uuauucgaca ggaggcucac aacaggc                                       87

<210> SEQ ID NO 75
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 75
gggagacaag aauaaacgcu caaauagggg guuaccugcc gacccagaa auaagcguga    60 uuuucgacag gaggcucaca acaggc                                        86

<210> SEQ ID NO 76
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 76
gggagacaag aauaaacgcu caauccugcc auagcgucuu caugucugac guuugaguuu    60
ccguucgaca ggaggcucac aacaggc                                       87

<210> SEQ ID NO 77
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 77
gggagacaag aauaaacgcu caauccuagg uugguccugc cacagcucaa agguuuagcu    60
ucauucgaca ggaggcucac aacaggc                                       87

<210> SEQ ID NO 78
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 78
gggagacaag aauaaacgcu caaacaugca gacaacccug ccuucugcgu gguuuaggag    60
uauucgacag gaggcucaca acaggc                                                86

<210> SEQ ID NO 79
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 79
gggagacaag aauaaacgcu caaaaccuca ggcgaccugc cgcugucuga aguucgagca      60
uaauucgaca ggaggcucac aacaggc                                         87

<210> SEQ ID NO 80
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 80
gggagacaag aauaaacgcu caaacucaag acccugccac uauguguuac ugaguaggag      60
cguuucgaca ggaggcucac aacaggc                                         87

<210> SEQ ID NO 81
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 81
gggagacaag aauaaacgcu caaauucgaa auacggguua aucccugcc uuuaacacga      60 cauucgacag gaggcucaca acaggc                                         86

<210> SEQ ID NO 82
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 82
gggagacaag aauaaacgcu caauguagcc gcaugucgag cagcaauucc ugccauugua      60
gguucgacag gaggcucaca acaggc                                         86

```
<210> SEQ ID NO 83
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 83
gggagacaag aauaaacgcu caacggugaa gaccucuauu aacaacauga ccugccugcg    60
uuguucgaca ggaggcucac aacaggc                                        87

<210> SEQ ID NO 84
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 84
gggagacaag aauaaacgcu caaucccacc cugccuuguc uguuugauag agacacuguc    60
cuuuucgaca ggaggcucac aacaggc                                        87

<210> SEQ ID NO 85
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 85
gggagacaag aauaaacgcu caagguuuga aagauugccu guagcuccaa aucuugguga    60
gcuuucgaca ggaggcucac aacaggc                                        87

<210> SEQ ID NO 86
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 86
gggagacaag aauaaacgcu caaucccgcc gauagcuucc acgaagaguu aucuguaaaa    60
caauucgaca ggaggcucac aacaggc                                        87

<210> SEQ ID NO 87
<211> LENGTH: 83
<212> TYPE: RNA
```

```
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(83)
<223> OTHER INFORMATION: All pyrimidines are 2' F.

<400> SEQUENCE: 87
gggagacaag aauaaacgcu caaugagcuc cugauuccaa accuauuccg uuucggguu      60 ucgacaggag gcucacaaca ggc                                            83

<210> SEQ ID NO 88
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 88
gggagacaag aauaaacgcu caaacuggac aagucaaucu cuccggcuug agacuugguu    60
uacuucgaca ggaggcucac aacaggc                                        87

<210> SEQ ID NO 89
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 89
gggagacaag aauaaacgcu caacgagcuc uugcuuccaa accuauucca gacguuucug    60
gguucgacag gaggcucaca acaggc                                         86

<210> SEQ ID NO 90
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 90
gggagacaag aauaaacgcu caagcgagcc uauugucuaa gaugcaccag gccuguuaag    60
cauuucgaca ggaggcucac aacaggc                                        87

<210> SEQ ID NO 91
<211> LENGTH: 84
<212> TYPE: RNA
<213> ORGANISM: Artificial Sequence
<220> FEATURE:
<223> OTHER INFORMATION: Description of Artificial Sequence: Synthetic
```

```
        Sequence
<220> FEATURE:
<221> NAME/KEY: modified_base
<222> LOCATION: (1)..(84)
<223> OTHER INFORMATION: All pyrimidines are 2' F.

<400> SEQUENCE: 91
gggagacaag aauaaacgcu caagccugua cggcgauuau gucuuuaccu uaacuguucc    60
uucgacagga ggcucacaac aggc                                          84

<210> SEQ ID NO 92
<211> LENGTH: 87
<212> TYPE: RNA
<213> ORGANISM: Artificial Sequence
<220> FEATURE:
<223> OTHER INFORMATION: Description of Artificial Sequence: Synthetic
        Sequence
<220> FEATURE:
<221> NAME/KEY: modified_base
<222> LOCATION: (1)..(87)
<223> OTHER INFORMATION: All pyrimidines are 2' F.

<400> SEQUENCE: 92
gggagacaag aauaaacgcu caauaccaau ggcacgaaua acugacuacc ccccaaaaug    60
gaauucgaca ggaggcucac aacaggc                                       87

<210> SEQ ID NO 93
<211> LENGTH: 87
<212> TYPE: RNA
<213> ORGANISM: Artificial Sequence
<220> FEATURE:
<223> OTHER INFORMATION: Description of Artificial Sequence: Synthetic
        Sequence
<220> FEATURE:
<221> NAME/KEY: modified_base
<222> LOCATION: (1)..(87)
<223> OTHER INFORMATION: All pyrimidines are 2' F.

<400> SEQUENCE: 93
gggagacaag aauaaacgcu caagcggggc uuugcucaag uguuugcaaa cgguaaauuc    60
cacuucgaca ggaggcucac aacaggc                                       87

<210> SEQ ID NO 94
<211> LENGTH: 87
<212> TYPE: RNA
<213> ORGANISM: Artificial Sequence
<220> FEATURE:
<223> OTHER INFORMATION: Description of Artificial Sequence: Synthetic
        Sequence
<220> FEATURE:
<221> NAME/KEY: modified_base
<222> LOCATION: (1)..(87)
<223> OTHER INFORMATION: All pyrimidines are 2' F.

<400> SEQUENCE: 94
gggagacaag aauaaacgcu caaccuaccg acguccgccg cuggguuaac cuguaaaguc    60
acuuucgaca ggaggcucac aacaggc                                       87

<210> SEQ ID NO 95
<211> LENGTH: 87
<212> TYPE: RNA
<213> ORGANISM: Artificial Sequence
<220> FEATURE:
<223> OTHER INFORMATION: Description of Artificial Sequence: Synthetic
        Sequence
<220> FEATURE:
<221> NAME/KEY: modified_base
```

<222> LOCATION: (1)..(87)
<223> OTHER INFORMATION: All pyrimidines are 2' F.

<400> SEQUENCE: 95
gggagacaag aauaaacgcu caagugaacc gauaagcgaa aguaguaccc cugcuugacu      60
acuuucgaca ggaggcucac aacaggc                                          87

<210> SEQ ID NO 96
<211> LENGTH: 88
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(88)
<223> OTHER INFORMATION: All pyrimidines are 2' F.

<400> SEQUENCE: 96
gggagacaag aauaaacgcu caaggagcuc cuaguuccaa accuauucca gaaguuuucu      60
ggguuucgac aggaggcuca caacaggc                                         88

<210> SEQ ID NO 97
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 97
gggagacaag aauaaacgcu caauaguacg cagucauagc ggggcaggga cuuucuccgu      60
gcauucgaca ggaggcucac aacaggc                                          87

<210> SEQ ID NO 98
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 98
gggagacaag aauaaacgcu caauuauacu gguaugccgc cgaccagaau uaauccaaug      60
cguuucgaca ggaggcucac aacaggc                                          87

<210> SEQ ID NO 99
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 99
gggagacaag aauaaacgcu caaugagcuc cugguuccaa accuauucca gacguuucag     60
gguuucgaca ggaggcucac aacaggc                                        87

<210> SEQ ID NO 100
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 100
gggagacaag aauaaacgcu caaucuggcc ugugacugua gucguuucuu cgaguuguga     60
cgcuucgaca ggaggcucac aacaggc                                        87

<210> SEQ ID NO 101
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 101
gggagacaag aauaaacgcu caacucaacg auguccaagg gcuuauauga gcgcguuacc     60
ccuucgacag gaggcucaca acaggc                                         86

<210> SEQ ID NO 102
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 102
gggagacaag aauaaacgcu caagcgagcc uauugucuaa gaugcgccaa gccuguaaag     60
cauuucgaca ggaggcucac aacaggc                                        87

<210> SEQ ID NO 103
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 103
gggagacaag aauaaacgcu caagacuagc cggccugaga uccuuguucg ccacacaugc     60
ugguucgaca ggaggcucac aacaggc                                        87

<210> SEQ ID NO 104
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 104
gggagacaag aauaaacgcu caacuucccc cgcaaacaca uguuuaguac ugggagacuu     60
ggguucgaca ggaggcucac aacaggc                                        87

<210> SEQ ID NO 105
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 105
gggagacaag aauaaacgcu caaugagcuc cugauuccga accuauucca gacguuucug     60
gguuucgaca ggaggcucac aacaggc                                        87

<210> SEQ ID NO 106
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2' F.

<400> SEQUENCE: 106
gggagacaag aauaaacgcu caacugaucc ucuugucauu guacaucucg caguucgaca     60
ggaggcucac aacaggc                                                   77

<210> SEQ ID NO 107
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 107
gggagacaag aauaaacgcu caauacuaag ccuaacaaaa gagcggauau uggcgcggca     60
cguucgacag gaggcucaca acaggc                                         86

<210> SEQ ID NO 108
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 108
gggagacaag aauaaacgcu caaagucuua guaguaccgc cugcuucuaa ccuugggcgc        60
uuuuucgaca ggaggcucac aacaggc                                           87

<210> SEQ ID NO 109
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 109
gggagacaag aauaaacgcu caaugauuuc augacuuaug ccgccggcau gacuucaaug        60
acguucgaca ggaggcucac aacaggc                                           87

<210> SEQ ID NO 110
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 110
gggagacaag aauaaacgcu caaucaaagg acggaagugc cugugcccga cuaaagaguu        60
gaguucgaca ggaggcucac aacaggc                                           87

<210> SEQ ID NO 111
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 111
gggagacaag aauaaacgcu caacuaucga ucguuuuuc auuccccu gaccaucgcc          60 uguucgacag gaggcucaca acaggc                                            86

<210> SEQ ID NO 112
<211> LENGTH: 87

<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 112
gggagacaag aauaaacgcu caauuguccc gcgcagaaac gugacaaauu uaacacgcac      60
cguuucgaca ggaggcucac aacaggc                                         87

<210> SEQ ID NO 113
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 113
gggagacaag aauaaacgcu caauucaacg uuguucaagg gcuuauauga gcgcguuaua      60
cccuucgaca ggaggcucac aacaggc                                         87

<210> SEQ ID NO 114
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 114
gggagacaag aauaaacgcu caaugauuuc augacuuaug ccgccggcau gacuucaaug      60
acguucgaca ggaggcucac aacaggc                                         87

<210> SEQ ID NO 115
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 115
gggagacaag aauaaacgcu caagcauuca aaauuugcga gaacgaauag aaguccgaga      60
gccuucgaca ggaggcucac aacaggc                                         87

<210> SEQ ID NO 116
<211> LENGTH: 87
<212> TYPE: RNA
<213> ORGANISM: Artificial Sequence
<220> FEATURE:

```
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 116
gggagacaag aauaaacgcu caagcgggau uuuccugauc aucccacuga uucggggccu      60
uacuucgaca ggaggcucac aacaggc                                         87

<210> SEQ ID NO 117
<211> LENGTH: 86
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(86)
<223> OTHER INFORMATION: All pyrimidines are 2' F.

<400> SEQUENCE: 117
gggagacaag aauaaacgcu caaucaaucu cggacuagac uaacgaccuu gguugacgcu      60
cauucgacag gaggcucaca acaggc                                          86

<210> SEQ ID NO 118
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2' F.

<400> SEQUENCE: 118
gggagacaag aauaaacgcu caacgccguu aucacgacgu gcguucuggg cgguacucgc      60
gcauucgaca ggaggcucac aacaggc                                         87
```